US012636287B2

(12) United States Patent
Wennogle et al.

(10) Patent No.: US 12,636,287 B2
(45) **Date of Patent: *May 26, 2026**

(54) ORGANIC COMPOUNDS

(71) Applicant: INTRA-CELLULAR THERAPIES, INC., New York, NY (US)

(72) Inventors: Lawrence P. Wennogle, Hillsborough, NJ (US); Joseph Hendrick, New York, NY (US); Robert Davis, San Diego, CA (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 1121 days.

This patent is subject to a terminal disclaimer.

(21) Appl. No.: 17/059,160

(22) PCT Filed: May 24, 2019

(86) PCT No.: PCT/US2019/033941

§ 371 (c)(1),
(2) Date: Nov. 25, 2020

(87) PCT Pub. No.: WO2019/227004

PCT Pub. Date: Nov. 28, 2019

(65) Prior Publication Data

US 2021/0205310 A1 Jul. 8, 2021

Related U.S. Application Data

(60) Provisional application No. 62/688,641, filed on Jun. 22, 2018, provisional application No. 62/676,638, filed on May 25, 2018.

(51) Int. Cl.
*A61K 31/519* (2006.01)
*A61P 35/00* (2006.01)

(52) U.S. Cl.
CPC ............ *A61K 31/519* (2013.01); *A61P 35/00* (2018.01)

(58) Field of Classification Search
CPC .............................. A61K 31/519; A61P 35/00
See application file for complete search history.

(56) References Cited

U.S. PATENT DOCUMENTS

| | | | |
|---|---|---|---|
| 4,690,935 A | 9/1987 | Taylor et al. | |
| 8,273,751 B2 | 9/2012 | Li | |
| 8,633,180 B2 | 1/2014 | Li et al. | |
| 8,664,207 B2 | 3/2014 | Li et al. | |
| 9,073,936 B2 | 7/2015 | Li et al. | |
| 9,545,406 B2 * | 1/2017 | Wennogle | A61K 31/53 |
| 9,708,294 B2 | 7/2017 | Li et al. | |
| 9,884,872 B2 | 2/2018 | Li et al. | |
| 10,092,575 B2 | 10/2018 | Branstetter et al. | |
| 10,150,774 B2 * | 12/2018 | Li | A61P 25/08 |
| 10,682,355 B2 * | 6/2020 | Wennogle | A61K 31/517 |
| 10,849,862 B2 | 12/2020 | Kawakami et al. | |
| 10,912,748 B2 | 2/2021 | Mohanlal et al. | |
| 11,291,666 B2 | 4/2022 | Snyder et al. | |
| 11,504,372 B2 * | 11/2022 | Wennogle | A61P 25/28 |
| 12,396,992 B2 * | 8/2025 | Snyder | A61K 31/519 |
| 2014/0128353 A1 | 5/2014 | Bannister et al. | |
| 2014/0235556 A1 | 8/2014 | Halse et al. | |
| 2015/0017267 A1 | 1/2015 | Guedes et al. | |
| 2016/0045617 A1 | 2/2016 | Lee et al. | |
| 2016/0324860 A1 | 11/2016 | Hendrick et al. | |
| 2016/0362489 A1 | 12/2016 | Yang | |
| 2020/0085782 A1 | 3/2020 | Gallatin et al. | |
| 2021/0338679 A1 | 11/2021 | Li et al. | |
| 2022/0072003 A1 | 3/2022 | Snyder et al. | |
| 2022/0354851 A1 | 11/2022 | Li et al. | |

FOREIGN PATENT DOCUMENTS

| | | | |
|---|---|---|---|
| CN | 107106563 A | 8/2017 | |
| RU | 2610094 C2 | 2/2017 | |
| WO | WO-2006/133261 A2 | 12/2006 | |
| WO | WO-2010/065148 A1 | 6/2010 | |
| WO | WO-2013/192229 A1 | 12/2013 | |
| WO | WO-2014/151409 A1 | 9/2014 | |
| WO | WO-2014145617 A2 * | 9/2014 | A61K 31/517 |
| WO | WO-2016/022893 A1 | 2/2016 | |
| WO | WO-2016/044667 A1 | 3/2016 | |
| WO | WO-2017/011831 A1 | 1/2017 | |
| WO | WO-2018/049417 A1 | 3/2018 | |
| WO | 2018/069312 A1 | 4/2018 | |
| WO | WO 2018/093591 A1 | 5/2018 | |
| WO | WO 2019/046778 A1 | 3/2019 | |
| WO | WO-2020/069043 A1 | 4/2020 | |
| WO | WO-2020/146384 A1 | 7/2020 | |

(Continued)

OTHER PUBLICATIONS

Savai et al. Targeting cancer with phosphodiesterase inhibitors Expert Opin. Investig. Drugs (2010) 19(1):117-131 (Year: 2010).*
Li et al. Discovery of Potent and Selective Inhibitors of Phosphodiesterase 1 for the Treatment of Cognitive Impairment Associated with Neurodegenerative and Neuropsychiatric Diseases, J. Med. Chem. 2016, 59, 1149-1164 (Year: 2016).*
Rowther et al. Cyclic nucleotide phosphodiesterase-1C (PDE1C) drives cell proliferation, migration and invasion in glioblastoma multiforme cells in vitro, Molecular Carcinogenesis, vol. 55, Issue Mar. 3, 2016 pp. 268-279, first published Jan. 25, 2015. (Year: 2015).*
Rowther et al. Cyclic Nucleotide Phosphodiesterase-1C (PDE1C) Drives Cell Proliferation, Migration and Invasion in Glioblastoma Multiforme Cells In Vitro, Molecular Carcinogenesis 55:268-279 (2016) (Year: 2016).*
Levy et al., "Phosphodiesterase Function and Endocrine Cells: Links to Human Disease and Roles in Tumor Development and Treatment," Current Opinion in Pharmacology, vol. 11, p. 689-697, (2011).

(Continued)

*Primary Examiner* — Adam C Milligan
*Assistant Examiner* — William Y Lee
(74) *Attorney, Agent, or Firm* — Hoxie & Associates LLC

(57) ABSTRACT

The disclosure relates to the combination of inhibitors of phosphodiesterase 1 (PDE1) useful for the treatment of certain cancers or tumors, such as gliomas. In another embodiment, the disclosure relates to the combination of inhibitors of PDE1 and an antitumor agent for the treatment of certain cancers or tumors, such as gliomas.

14 Claims, 5 Drawing Sheets

(56) References Cited

FOREIGN PATENT DOCUMENTS

| | | | |
|---|---|---|---|
| WO | WO-2021/046250 | A1 | 3/2021 |
| WO | WO-2023/173131 | A2 | 9/2023 |

OTHER PUBLICATIONS

Snyder et al., "Suppression of CNS Inflammation by Phosphodiesterase-1 (PDE1) Inhibitors: Toward New Treatments for Neurodegenerative Diseases," Database Embase, Database Accession No. EMB-620612543, Alzheimer's Association International Conference AAIC 2017 in London, 2 pages, Abstract only.
Abusnina et al., "Anti-proliferative Effect of Curcumin on Melanoma Cells is Mediated by PDE1A Inhibition that Regulates the Epigenetic Integrator UHRF1," Mol. Nutr. Food Res., vol. 55, pp. 1677-1689, (2011); doi: 10.1002/mnfr.201100307.
Ahlström et al., "Cyclic Nucleotide Phosphodiesterases (PDEs) in Human Osteoblastic Cells; The Effect of PDE Inhibition on cAMP Accumulation," Cell Mol Biol Lett, vol. 10, No. 10, pp. 305-319, (2005).
Ahmad et al., "Cyclic Nucleotide Phosphodiesterases: Important Signaling Modulators and Therapeutic Targets," Oral Diseases, vol. 21, pp. e25-e50, (2015); doi: 10.1111/odi.12275.
Almahariq et al., "Pharmacological Inhibition and Genetic Knockdown of Exchange Protein Directly Activated by cAMP 1 Reduce Pancreatic Cancer Metastasis In Vivo," Molecular Pharmacology, vol. 87, No. 2, pp. 142-149, (2015), DOI: https://doi.org/10.1124/mol.114.095158.
Argyle et al., "Targeting Macrophage-Recruiting Chemokines as a Novel Therapeutic Strategy to Prevent the Progression of Solid Tumors," Frontiers in Immunology, vol. 9, 15 pages, (2018); doi: 10.3389/fimmu.2018.02629.
Boyd et al., "cAMP-Phosphodiesterase PDE4D as a Target for Colon Cancer Therapy," The FASEB Journal, vol. 31, No. 1, 2 pages, (2017).
Brodbelt et al., "Glioblastoma in England: 2007-2011", Eur. J. Cancer, vol. 51, pp. 533-542, (2015).
Chen et al., "cAMP Inhibits Cell Migration by Interfering with Rac-induced Lamellipodium Formation," Journal of Biological Chemistry, vol. 283, No. 20, p. 13799-13805, (2008), DOI: 10.1074/jbc.M800555200.
Coussens et al., "Inflammation and Cancer," Nature, vol. 420, No. 6917, pp. 860-867, (2002), DOI: 10.1038/nature01322.
Daniel et al., "Sensitivity of GBM Cells to cAMP Agonist-mediated Apoptosis Correlates with CD44 Expression and Agonist Resistance with MAPK Signaling," Cell Death and Disease, vol. 7, No. e2494, 11 pages, (2016), DOI: 10.1038/cddis.2016.393.
Insel et al., "Cyclic AMP is Both a Pro-apoptotic and Anti-apoptotic Second Messenger," Acta Physiol (Oxf), vol. 204, No. 2, pp. 277-287, (2012), DOI: 10.1111/j.1748-1716.2011.02273.x.
Jang et al., "Adaptation of cAMP Signaling System in SH-SY5Y Neuroblastoma Cells Following Expression of a Constitutively Active Stimulatory G Protein Alpha, Q227L Gsα," Exp Mol Med, vol. 33, No. 1, pp. 37-45, (2001).
Jiang et al., "Expression and Regulation of mRNA for Distinct Isoforms of cAMP-Specific PDE-4 in Mitogen-Stimulated and Leukemic Human Lymphocytes," Cell Biochem Biophys, vol. 28, pp. 135-160, (1998).
Kim et al., "Antiinflammatory cAMP Signaling and Cell Migration Genes Co-opted by the Anthrax Bacillus," PNAS, vol. 105, No. 16, pp. 6150-6155, (2008).
Marko et al., "Cyclic 3',5'-nucleotide Phosphodiesterases: Potential Targets for Anticancer Therapy," Chem Res Toxicol, vol. 13, pp. 944-948, (2000).
Medina, A, "Therapeutic Utility of Phosphodiesterase Type I Inhibitors in Neurological Conditions," Frontiers in Neuroscience, vol. 5, No. 21, pp. 1-5, (2011), DOI: 10.3389/fnins.2011.00021.
Pantziarka et al., "Repurposing Drugs in Oncology (ReDO)—Selective PDE5 Inhibitors as Anti-Cancer Agents," ECancer, vol. 12, No. 824, 22 pages, (2018).
Peng et al., "Inhibitors of Phosphodiesterase as Cancer Therapeutics," European Journal of Medicinal Chemistry, vol. 150, pp. 742-756, (2018).
Rowther et al., "Cyclic Nucleotide Phosphodiesterase-1C (PDE1C) Drives Cell Proliferation Migration and Invasion in Glioblastoma Multiforme Cells In Vitro," Molecular Carcinogenesis, vol. 55, pp. 268-279, (2016), DOI: 10.1002/mc.22276.
Rybalkin et al., "Calmodulin-stimulated Cyclic Nucleotide Phosphodiesterase (PDE1C) is Induced in Human Arterial Smooth Muscle Cells of the Synthetic, Proliferative Phenotype," J Clin Invest, vol. 100, No. 10, pp. 2611-2621, (1997).
Savai et al., "Targeting Cancer with Phosphodiesterase Inhibitors," Expert Opin. Investig. Drugs, vol. 19, No. 1, pp. 117-131, (2010), DOI: 10.1517/13543780903485642.
Shimizu et al., "Characterization of Phosphodiesterase 1 in Human Malignant Melanoma Cell Lines," AntiCancer Research, vol. 29, pp. 1119-1122, (2009).
Shiri et al., "Dendrosomal Curcumin Suppresses Metastatic Breast Cancer in Mice by Changing M1/M2 Macrophage Balance in the Tumor Microenvironment," Asian Pac J Cancer Prev., vol. 16, No. 9, pp. 3917-3922, (2015).
Soon, L, "A Discourse on Cancer Cell Chemotaxis: Where to From Here?", IUBMB Life, vol. 59, No. 2, pp. 60-67, (2007), DOI: 10.1080/15216540701201033.
Stupp et al., "Radiotherapy Plus Concomitant and Adjuvant Temozolomide for Glioblastoma", N Engl J Med, vol. 352, No. 10, pp. 987-996, (2005).
Touat et al., "Glioblastoma Targeted Therapy: Updated Approaches from Recent Biological Insights," Ann. Oncol., vol. 28, No. 7, pp. 1457-1472, (2017).
Vitale et al., "A New Therapeutic Strategy Against Cancer: cAMP Elevating Drugs and Leptin," Cancer Biology & Therapy, vol. 8, No. 12, pp. 1191-1193, (2009), DOI: 10.4161/cbt.8.12.8937.
Watanabe et al., "Phosphodiesterase 4 Regulates the Migration of B16-F10 Melanoma Cells," Exp Ther Med, vol. 4, pp. 205-210, (2012).
"Gene expression," Wikipedia, 17 pages, (2017); accessed on Jul. 18, 2019 at https://en.wikipedia.org/w/index.php?title=Gene_expression&oldid=803718522.
Zong et al., "The Cellular Origin for Malignant Glioma and Prospects for Clinical Advancements," Expert Rev Mol Diagn., vol. 12, No. 4, pp. 383-394, (2012), DOI: 10.1586/erm.12.30.
Zhao et al., "Recent Advances in the Study of Ca2+/CaM-activated Phosphodiesterases: Expression and Physiological Functions," Adv Second Messenger Phosphoprotein Res, vol. 31, p. 237-251, (1997).
Al-Faleq, E. et al., "Heterocyclic o-Aminonitriles: Preparation of Pyrazolo[3,4-d]-pyrimidines with Modification of the substituents at the 1-position," Molecules, vol. 6, pp. 621-638, (2001).
Hayakawa, T. et al., "Enhanced anti-tumor effects of the PD-1/PD-L1 blockade by combining a highly absorptive form of NF-κB/STAT3 inhibitor curcumin," Journal for Immuno Therapy of Cancer, vol. 2, Suppl. 3, p. P210, (2014).
Johnson, J. et al., "Curcumin for chemoprevention of colon cancer," Cancer Letters, vol. 255, pp. 170-181, (2007).
Martinez, F. et al., "Genetic Programs Expressed in Resting and IL-4 Alternatively Activated Mouse and Human Macrophages: Similarities and Differences," Blood, vol. 121, No. 9, 13 pages, (2013).
Mietto, B. et al., "Role of IL-10 in Resolution of Inflammation and Functional Recovery after Peripheral Nerve Injury," The Journal of Neuroscience, vol. 35, No. 50, pp. 16431-16442, (2015).
Yue, G. et al., "Combined therapy using bevacizumab and turmeric ethanolic extract (with absorbable curcumin) exhibited beneficial efficacy in colon cancer mice," Pharmacological Research, vol. 111, pp. 43-57, (2016).
Barakat, A. et al., "Substituted spirooxindole derivatives as potent anticancer agents through inhibition of phosphodiesterase 1," RSC Advances, vol. 8, No. 26, pp. 14335-14346, 12 pages, (2018).

(56) References Cited

OTHER PUBLICATIONS

Dou, H. et al., "Curcumin Suppresses the Colon Cancer Proliferation by Inhibiting Wnt/β-Catenin Pathways via miR-130a," Frontiers in Pharmacology, vol. 8, Article 877, 9 pages, (2017).
Fajardo, A. et al., "The Role of Cyclic Nucleotide Signaling Pathways in Cancer: Targets for Prevention and Treatment," Cancers, vol. 6, pp. 436-458, (2014).
Snyder, G. et al., "Preclinical Profile of ITI-214, an Inhibitor of Phosphodiesterase 1, for Enhancement of Memory Performance in Rats," Psychopharmacology, vol. 213, pp. 3113-3124, (2016).
Swart, M. et al., "Combination Approaches with Immune-Checkpoint Blockade in Cancer Therapy," Frontiers in Oncology, vol. 6, Article 233, 16 pages, (2016).
Tong, W. et al., "Curcumin suppresses colon cancer cell invasion via AMPK-induced inhibition of NF-KB, uPA activator and MMP9," Oncology Letters, vol. 12, No. 5, pp. 4139-4146, 8 pages, (2016).

* cited by examiner

Cell Proliferation of Cultures Post siRNA Treatments

ORGANIC COMPOUNDS

CROSS-REFERENCE TO RELATED APPLICATIONS

This application is a U.S. National Stage Application under 35 U.S.C. § 371 of International Application No. PCT/US2019/033941, which was filed on May 24, 2019, which claims priority to and the benefit of U.S. Provisional Application Ser. No. 62/676,638, which was filed on May 25, 2018, and U.S. Provisional Application Ser. No. 62/688,641, which was filed on Jun. 22, 2018, the contents of each of which are hereby incorporated by reference in their entireties.

FIELD OF DISCLOSURE

The field relates to inhibitors of phosphodiesterase 1 (PDE1) useful for the treatment of certain cancers and tumors, such as tumors of the the central nervous system. The field further relates to the administration of inhibitors of phosphodiesterase 1 (PDE1) for the for the treatment of certain cancers and tumors, such as tumors of the the central nervous system, or for the treatment of related conditions characterized by an increased expression in PDE1.

BACKGROUND OF THE DISCLOSURE

Glioblastoma is the most common malignant brain tumour in adults, its occurrence accounting for more than half of all primary brain tumours in a frequency of 2 to 3 per 100,000 in western developed countries. Prognosis is almost universally poor with a median survival of 6-9 months and five-year survival rates of less than 3%. Brodbelt A, et al.; (UK) National Cancer Information Network Brain Tumour Group. Glioblastoma in England: 2007-2011. Eur. J. Cancer. 2015 March; 51(4): 533-42.

Glioblastoma is an aggressive tumour that is characterised by rapid growth and invasion into the normal brain. The efficacy of current treatments is hampered by the need to preserve normal brain function during surgery, by the tumours' intrinsic resistance to radiotherapy, and the inability of many drugs to penetrate the blood brain barrier. There has been little improvement for adult glioblastoma patients during the last three decades as successive Phase III trials of targeted agents have failed to improve survival (Touat M, et al., Glioblastoma targeted therapy: updated approaches from recent biological insights. Ann. Oncol. 2017 Jul. 1; 28(7): 1457-1472) and temozolamide (an alkylating compound able to cross the blood brain barrier) remains one of the only effective chemotherapeutic agents available for treating glioblastoma. Even with maximal treatment of debulking surgery, radiotherapy and temozolomide, median survival is only 14.6 months. Stupp R, et al., Radiotherapy plus concomitant and adjuvant temozolomide for glioblastoma; N Engl J Med. 2005 Mar. 10; 352(10): 987-96.

Currently, there is a largely unmet need for an effective way of treating tumors of the central nervous system, such as glioblastoma multiforme. Improved therapeutic compositions and methods for the treatment of such conditions are urgently required.

Eleven families of phosphodiesterases (PDEs) have been identified but only PDEs in Family I, the Ca2+/calmodulin-dependent phosphodiesterases (CaM-PDEs), which are activated by Ca2+/calmodulin and have been shown to mediate the calcium and cyclic nucleotide (e.g. cGMP and cAMP) signaling pathways. The three known CaM-PDE genes, PDE1A, PDE1B, and PDE1C, are all expressed in central nervous system tissue. PDE1A is expressed in the brain, lung and heart. PDE1B is primarily expressed in the central nervous system, but it is also detected in monocytes and neutrophils and has been shown to be involved in inflammatory responses of these cells. PDE1C is expressed in olfactory epithelium, cerebellar granule cells, striatum, heart, and vascular smooth muscle. PDE1C has been demonstrated to be a major regulator of smooth muscle proliferation in human smooth muscle.

Cyclic nucleotide phosphodiesterases down-regulate intracellular CAMP and cGMP signaling by hydrolyzing these cyclic nucleotides to their respective 5'-monophosphates (5'AMP and 5'GMP), which are inactive in terms of intra-cellular signaling pathways. Both cAMP and cGMP are central intracellular second-messengers and they play roles in regulating numerous cellular functions. PDE1A and PDE1B preferentially hydrolyze cGMP over CAMP, while PDE1C shows approximately equal cGMP and cAMP hydrolysis.

With respect to PDE1C in particular, recent evidences indicate that PDE1C is a proliferation associated gene, since it is expressed exclusively in proliferating vascular smooth muscle cells. (Rybalkin S D, et al., Calmodulin-stimulated cyclic nucleotide phosphodiesterase (PDE1C) is induced in human arterial smooth muscle cells of the synthetic, proliferative phenotype. J Clin Invest 1997; 100:2611-2621.) In addition, there have been sporadic reports of PDE1C expression along with other PDE subtypes in experimental tumor models such as melanoma (Watanabe Y, et al., Phosphodiesterase 4 regulates the migration of B16-F10 melanoma cells. Exp Ther Med 2012; 4:205-210.), neuroblastoma (Jang I S, Juhnn Y S. Adaptation of cAMP signaling system in SH-SY5Y neuroblastoma cells following expression of a constitutively active timulatory G protein alpha, Q227L Gsalpha. Exp Mol Med 2001; 33:37-45), and osteosarcoma (Ahlström M, et al., Cyclic nucleotide phosphodiesterases (PDEs) in human osteoblastic cells; the effect of PDE inhibition on cAMP accumulation. Cell Mol Biol Lett 2005; 10:305-319).

Past studies have shown that inhibition of the PDE1 (specifically the isoform PDE1B) induces apoptosis in human leukemia cells. Jiang X, Paskind M, Weltzien R, Epstein P M. Expression and regulation of mRNA for distinct isoforms of mitogen-stimulated and leukemic human lymphocytes. Cell Biochem Biophys 1998; 28:135-60. Studies have also shown that, five out of six human glioblastoma cell lines from the National Cancer Institute show high PDE1 expression (predominantly PDE1C) and only minor PDE4 expression. Marko D, Pahlke G, Merz K H, Eisenbrand G. Cyclic 3',5'-nucleotide phosphodiesterases: potential targets for antitumor therapy. Chem Res Toxicol 2000; 13:944-8. Likewise, PDE1C mRNA is overexpressed in human malignant melanoma-associated antigen (MAA) cells, and growth is inhibited by the non-selective PDE1 inhibitor vinpocetine. Zhao A Z, et al., Recent advances in the study of Ca2+/CaM-activated phosphodiesterases: expression and physiological functions. Adv Second Messenger Phosphoprotein Res 1997; 31:237-51. More recent studies show that PDE1C is significantly overexpressed in 20% of glioblastoma compared to normal human brain and siRNA mediated silencing of PDE1C inhibits proliferation (45-50%) and invasion (40-60%) in patient-derived cell cultures of glioblastoma. Rowther F B, et al., Cyclic nucleotide phosphodiesterase-1C (PDE1C) drives cell proliferation, migration and invasion in glioblastoma multiforme cells in vitro. Mol Carcinog. 2016 March; 55(3): 268-79.

Tumor-promoting cellular proliferation, migration, tissue invasion and inflammation are considered enabling characteristics of cancer development. Each of these processes are time-dependent, variable and complex involving a multitude of signal transduction pathways. It is believed that multi-targeted agents produce greater benefits than those observed with single-targeted therapies, have acceptable tolerability profiles, and are active against a broader range of tumor types. Regulation of cyclic nucleotide signaling is properly regarded as a composite of multiple component pathways involved in diverse aspects of tumor cell function. The impairment of cAMP generation has been described in various cancer pathologies. Attempts to directly regulate cyclic nucleotides in cancer cells, while being antiproliferative have not been productive, owing to high cytotoxicity. New, safer and selective strategies for modulating cAMP in cancer cells are needed.

SUMMARY OF THE DISCLOSURE

The inventors have previously shown that inhibition of PDE1 activity using the presently disclosed compounds can safely restore cAMP function in a wide spectrum of pathological conditions, including models of neurodegeneration and neuroinflammation, heart failure, pulmonary hypertension and peripheral inflammation and in humans with certain diseases. More recently, the inventors have shown that PDE1 inhibitors obstruct cellular migration of microglia and monocytes. Recent evidence indicates that PDE1, particularly the PDE1C isoform, is over expressed in experimental tumor models such as melanoma, neuroblastoma, and osteosarcoma. In addition, focal genomic over representation of PDE1C in Glioblastoma Multiforme (GBM) cells has been demonstrated. Genomic gain of PDE1C is associated with increased expression in GBM-derived cell cultures and is essential for driving cell proliferation, migration and invasion in cancer cells.

Many types of cancer cells over express PDE1 activity, which is identified through various biomarkers, such as increased RNA expression, DNA copy number, PDE1 binding (PET or radio-isotope retention of PDE1 inhibitor molecules) or enzymatic activity. These cancer cells also exhibit low levels of CAMP, which can be increased by PDE1 inhibitors. Such characteristics can be treated with PDE-1 inhibitors alone or in combination with chemotherapeutics, gene therapeutics and/or immunologic approaches. Inhibiting PDE1 provokes apoptotic cell death, prevents migration, limits metastasis, and reduces inflammation. In this way, PDE1 inhibitors are synergistic with chemotherapeutics and immunologic approaches.

In addition, many gene therapies and antibody approaches are known to cause cytokines release syndrome (CRS). CRS is caused by a large, rapid release of cytokines into the blood from immune cells affected by the immunotherapy. PDE1 has previously been shown to reduce the expression of the inflammatory cytokines IL1β, TNFα, and Ccl2. See International Patent Publication WO2018/049147. PDE1 inhibition is useful prophylactically in these cases, and a PDE1 inhibitor may be administered together with corticosteroids and antihistamines to prevent CRS Without being bound by theory, it is believed that impaired cAMP (or cGMP) generation arises from overexpression of PDE1 isoforms in various cancer pathologies. Inhibition of selective PDE1 isoforms, which raises the levels of intracellular cAMP (and/or cGMP), induces apoptosis and cell cycle arrest in a broad spectrum of tumor cells and regulates the tumor microenvironment preventing cellular migration, inflammation, and tissue invasion. Therefore, the development and clinical application of inhibitors specific for individual PDE1 and its isoforms, particularly PDE1c, may selectively restore normal intracellular signaling, providing antitumor therapy with reduced adverse effects.

The present disclosure relates to the use of a PDE1 inhibitor for the treatment of a cancer or tumor, including, e.g., carcinomas, melanomas, and astrocytomas. In a preferred embodiment, the PDE1 inhibitor is selective. Previous studies have demonstrated that PDE1 (i.e., PDE1C) is significantly overexpressed in glioblastoma patients compared to healthy patients (i.e., those not suffering from glioblastoma). siRNA mediated silencing of PDE1C has been shown to inhibit proliferation and invasion in patient-derived cell cultures of glioblastoma. Without being bound by any theory, inhibition of PDE1, such as PDE1C, may be effective in the therapeutic intervention of certain cancers or tumors, such as glioblastoma.

Treating brain tumors in particular requires compounds possessing the ability to cross the blood brain barrier. The compounds of the present disclosure are potent inhibitors of PDE1. In particular the presently disclosed compounds show high selectivity for both PDE1A and PDE1C isoforms and are capable of penetrating the blood brain barrier.

Therefore, in various embodiments, the present disclosure provides for methods of treating a condition selected from a cancer or tumor comprising administering a pharmaceutically acceptable amount of a PDE1 inhibitor as disclosed herein to a subject in need thereof. In some embodiments, the cancer or tumor is a glioma, leukemia, melanoma, neuroblastoma, or osteosarcoma. In some embodiments, the cancer or tumor is an astrocytoma, such as glioblastoma multiforme. In some embodiments, the PDE1 inhibitor is administered in combination with an antitumor agent.

In various embodiments, the present disclosure provides for methods of inhibiting the proliferation, migration and/or invasion of tumorous cells comprising administering a pharmaceutically acceptable amount of a PDE1 inhibitor as disclosed herein to a subject in need thereof. In some embodiments, the cancer or tumor is a glioma, leukemia, melanoma, neuroblastoma, or osteosarcoma. In some embodiments, the cancer or tumor is an astrocytoma, such as glioblastoma multiforme. In some embodiments, the PDE1 inhibitor is administered in combination with an antitumor agent.

In various embodiments, the present application provides for a method of treating a glioma comprising administering a pharmaceutically acceptable amount of a PDE1 inhibitor to a subject in need thereof. In some embodiments, the cancer or tumor is an astrocytoma, such as glioblastoma multiforme. In some embodiments, the PDE1 inhibitor is administered in combination with an antitumor agent.

In another aspect, the present disclosure also includes a PDE1 inhibitor of Formula I, Ia, II, III and/or IV described hereinbelow in free or salt form. In a preferred embodiment, the PDE1 inhibitor is a selective PDE1 inhibitor. In another embodiment, the disclosure further provides a pharmaceutical composition comprising a PDE1 inhibitor in free or pharmaceutically acceptable salt form, in admixture with a pharmaceutically acceptable carrier.

In various embodiments, the present disclosure provides for combination therapies comprising a PDE1 inhibitor of Formula I, Ia, II, III and/or IV described hereinbelow in free or salt form and an antitumor agent. The combination therapy can be used in conjunction with any of the methods disclosed herein. In some embodiments, the antitumor agent is administered concurrently with, before or after administration of the PDE1 inhibitor.

In various embodiments, the present disclosure also provides for pharmaceutical compositions comprising Compounds of the present disclosure prepared using conventional diluents or excipients and techniques known in the art. Thus, oral dosage forms may include tablets, capsules, solutions, suspensions and the like.

In various embodiments, the present disclosure also provides PDE1 inhibitors according to Formula I, Ia, II, III and/or IV described hereinbelow in free or salt form for use in the treatment of a condition selected from a cancer or tumor, inhibiting the proliferation, migration and/or invasion of tumorous cells, or treating a glioma.

DETAILED DESCRIPTION OF THE DISCLOSURE

Figure 1:
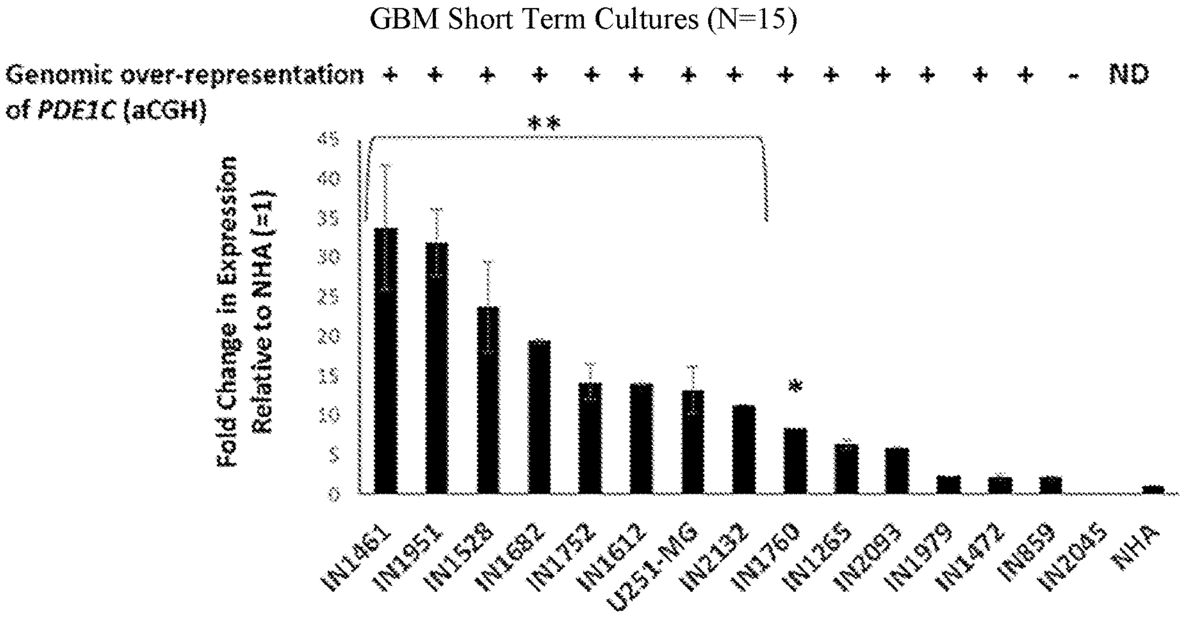
FIG. 1 shows PDE1C expression in glioblastoma multiforme (GBM) short term cell cultures.
Figure 2:
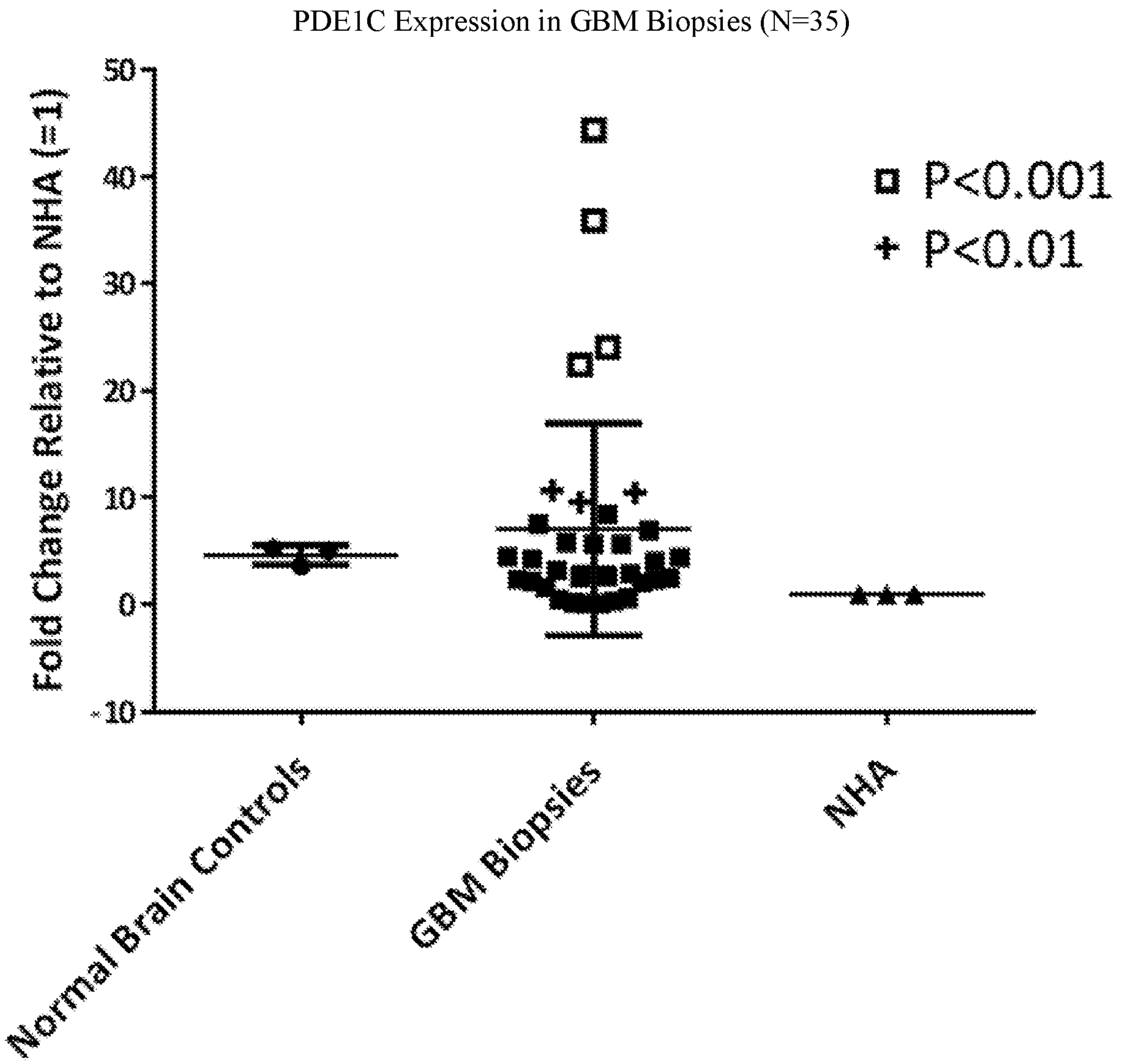
FIG. 2 shows the change in PDE1C expression in freshly frozen GBM biopsy specimens presented in relation to normal human astrocytes.

Compounds for Use in the Methods of the Disclosure

In one embodiment, the PDE1 inhibitors for use in the methods of treatment and prophylaxis described herein are selective PDE1 inhibitors.

PDE1 Inhibitors

In one embodiment the invention provides that the PDE1 inhibitors for use in the methods of treatment and prophylaxis described herein are compounds of Formula I:

Formula I

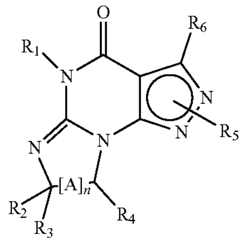

wherein (i) $R_1$ is H or $C_{1-4}$ alkyl (e.g., methyl);

(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero) arylalkoxy, or (optionally hetero) arylalkyl; or $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);

(iii) $R_5$ is a substituted heteroarylalkyl, e.g., substituted with haloalkyl; or $R_5$ is attached to one of the nitrogens on the pyrazolo portion of Formula I and is a moiety of Formula A Formula A

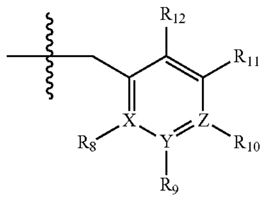

wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl) optionally substituted with halogen, or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and (iv) $R_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl)amino (e.g., N-phenyl-N-(1,1'-biphen-4-ylmethyl)amino); and (v) n=0 or 1; (v)

(vi) when n=1, A is —$C(R_{13}R_{14})$— wherein $R_{13}$ and $R_{14}$, are, independently, H or $C_{1-4}$ alkyl, aryl, heteroaryl, (optionally hetero) arylalkoxy or (optionally hetero) arylalkyl;

in free, salt or prodrug form, including its enantiomers, diastereoisomers and racemates.

In another embodiment the invention provides that the PDE1 inhibitors for use in the methods as described herein are Formula 1a:

Formula Ia

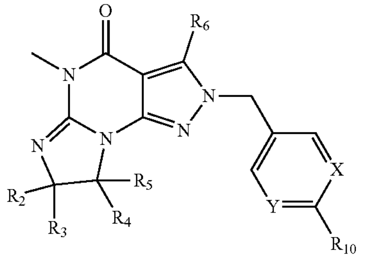

wherein (i) $R_2$ and $R_5$ are independently H or hydroxy and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ and $R_5$ are each H; or $R_2$, $R_4$ and $R_5$ are H and $R_3$ is isopropyl [pref. the carbon carrying $R_3$ having the R configuration];

(ii) $R_6$ is (optionally halo-substituted) phenylamino, (optionally halo-substituted) benzylamino, $C_{1-4}$alkyl, or $C_{1-4}$alkyl sulfide; for example, phenylamino or 4-fluorophenylamino;

(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl (for example 6-fluoropyrid-2-yl), or thiadiazolyl (e.g., 1,2,3-thiadiazol-4-yl); and X and Y are independently C or N, in free, pharmaceutically acceptable salt or prodrug form, including its enantiomers, diastereoisomers and racemates.

In another embodiment the invention provides that the PDE1 inhibitors for use in the methods of treatment and prophylaxis described herein are compounds of Formula II:

Formula II

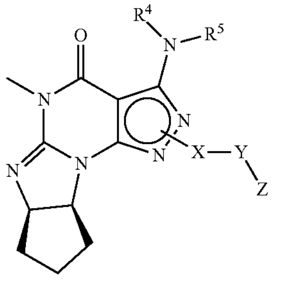

(i) X is $C_{1-6}$alkylene (e.g., methylene, ethylene or prop-2-yn-1-ylene);

(ii) Y is a single bond, alkynylene (e.g., —C≡C—), arylene (e.g., phenylene) or heteroarylene (e.g., pyridylene);

(iii) Z is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), —C(O)—$R^1$, —$N(R^2)(R^3)$, or $C_{3-7}$cycloalkyl optionally containing at least one atom selected from a group consisting of N or O (e.g., cyclopentyl, cyclohexyl, tetrahydro-2H-pyran-4-yl, or morpholinyl);

(iv) $R^1$ is $C_{1-6}$alkyl, halo$C_{1-6}$alkyl, —OH or —O$C_{1-6}$alkyl (e.g., —$OCH_3$);

(v) $R^2$ and $R^3$ are independently H or $C_{1-6}$alkyl;

(vi) $R^4$ and $R^5$ are independently H, $C_{1-6}$alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or $C_{1-6}$alkoxy;

(vii) wherein X, Y and Z are independently and optionally substituted with one or more halo (e.g., F, Cl or Br), $C_{1-6}$alkyl (e.g., methyl), halo$C_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-6}$alkyl (e.g., 5-trifluoromethylpyrid-2-yl) or $C_{1-6}$-alkyl (e.g., 5-methylpyrid-2-yl), or Z is aryl, e.g., phenyl, substituted with one or more halo (e.g., 4-fluorophenyl), in free, salt or prodrug form.

In yet another embodiment the invention provides that the PDE1 inhibitors for use in the methods of treatment and prophylaxis described herein are Formula III:

Formula III

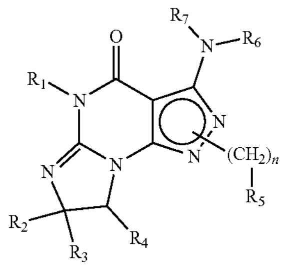

wherein (i) R1 is H or $C_{1-4}$ alkyl (e.g., methyl or ethyl);

(ii) $R_2$ and $R_3$ are independently H or $C_{1-6}$ alkyl (e.g., methyl or ethyl);

(iii) $R_4$ is H or $C_{1-4}$ alkyl (e.g., methyl or ethyl);

(iv) $R_5$ is aryl (e.g., phenyl) optionally substituted with one or more groups independently selected from —C(═O)—$C_1$-6 alkyl (e.g., —C(═O)—$CH_3$) and $C_{1-6}$-hydroxyalkyl (e.g., 1-hydroxyethyl);

(v) $R_6$ and $R_7$ are independently H or aryl (e.g., phenyl) optionally substituted with one or more groups independently selected from $C_{1-6}$ alkyl (e.g., methyl or ethyl) and halogen (e.g., F or Cl), for example unsubstituted phenyl or phenyl substituted with one or more halogen (e.g., F) or phenyl substituted with one or more $C_{1-6}$ alkyl and one or more halogen or phenyl substituted with one $C_{1-6}$ alkyl and one halogen, for example 4-fluorophenyl or 3,4-difluorophenyl or 4-fluoro-3-methylphenyl; and (vi) n is 1, 2, 3, or 4, in free or salt form.

In yet another embodiment the invention provides that the PDE1 inhibitors for use in the methods of treatment and prophylaxis described herein are Formula IV Formula IV

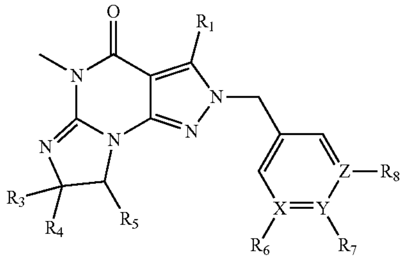

in free or salt form, wherein (i) $R_1$ is $C_{1-4}$alkyl (e.g., methyl or ethyl), or —$NH(R_2)$, wherein $R_2$ is phenyl optionally substituted with halo (e.g., fluoro), for example, 4-fluorophenyl;

(ii) X, Y and Z are, independently, N or C;

(iii) $R_3$, $R_4$ and $R_5$ are independently H or $C_{1-4}$alkyl (e.g., methyl); or $R_3$ is H and $R_4$ and $R_5$ together form a tri-methylene bridge (pref. wherein the $R_4$ and $R_5$ together have the cis configuration, e.g., where the carbons carrying $R_4$ and $R_5$ have the R and S configurations, respectively), (iv) $R_6$, $R_7$ and $R_5$ are independently:

H, $C_{1-4}$alkyl (e.g., methyl), pyrid-2-yl substituted with hydroxy, or

—$S(O)_2$—$NH_2$;

(v) Provided that when X, Y and/or Z are N, then $R_6$, $R_7$ and/or $R_8$, respectively, are not present; and when X, Y and Z are all C, then at least one of $R_6$, $R_7$ or $R_8$ is —$S(O)_2$—$NH_2$ or pyrid-2-yl substituted with hydroxy.

In one embodiment the invention provides administration of a PDE1 inhibitor for treatment or prophylaxis of inflammation or an inflammatory related disease or disorder, wherein the inhibitor is a compound according to the following:

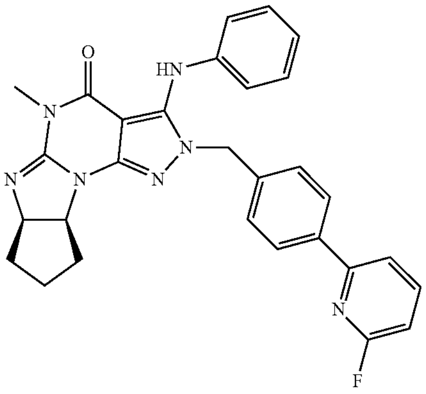 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

In still another embodiment, the invention provides administration of a PDE1 inhibitor for treatment or prophylaxis of inflammation or an inflammatory related disease or disorder, wherein the inhibitor is a compound according to the following:

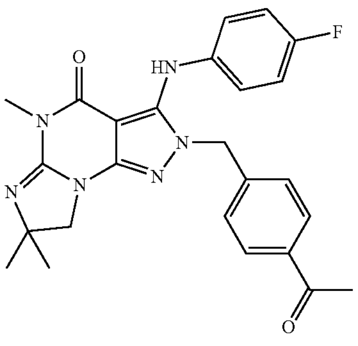 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

In still another embodiment, the invention provides administration of a PDE1 inhibitor for treatment or prophylaxis of inflammation or an inflammatory related disease or disorder, wherein the inhibitor is a compound according to the following:

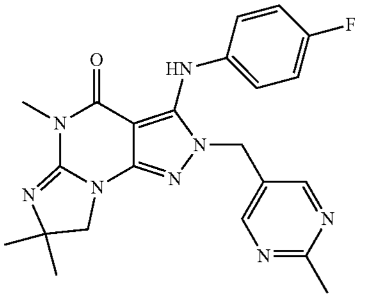 [SMILES: Cc1ncc(Cn2nc3c(c2Nc2ccc(F)cc2)C(=O)N(C)C2=NC(C)(C)CN23)cn1]

in free or pharmaceutically acceptable salt form.

In still another embodiment, the invention provides administration of a PDE1 inhibitor for treatment or prophylaxis of inflammation or an inflammatory related disease or disorder, wherein the inhibitor is a compound according to the following:

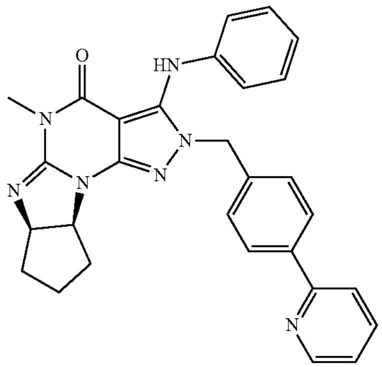 [SMILES: CN1C(=O)c2c(nn(Cc3ccc(-c4ccccn4)cc3)c2Nc2ccccc2)N2C1=N[C@@H]1CCC[C@@H]12]

in free or pharmaceutically acceptable salt form.

In still another embodiment, the invention provides administration of a PDE1 inhibitor for treatment or prophylaxis of inflammation or an inflammatory related disease or disorder, wherein the inhibitor is a compound according to the following:

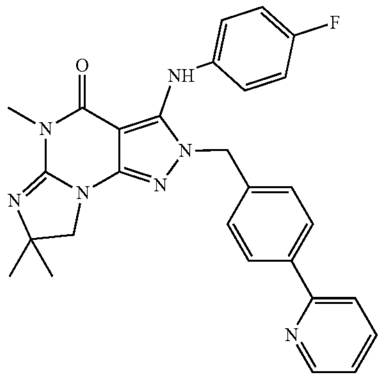 [SMILES: CN1C(=O)c2c(nn(Cc3ccc(-c4ccccn4)cc3)c2Nc2ccc(F)cc2)N2CC(C)(C)N=C12]

in free or pharmaceutically acceptable salt form.

In one embodiment, selective PDE1 inhibitors of any of the preceding formulae (e.g., Formula I, Ia, II, III and/or IV) are compounds that inhibit phosphodiesterase-mediated (e.g., PDE1-mediated, especially PDE1B-mediated) hydrolysis of cGMP, e.g., the preferred compounds have an $IC_{50}$ of less than 1 μM, preferably less than 500 nM, preferably less than 50 nM, and preferably less than 5 nM in an immobilized-metal affinity particle reagent PDE assay, in free or salt form.

In other embodiments, the the invention provides administration of a PDE1 inhibitor for treatment of a condition selected from a cancer or tumor; for inhibiting the proliferation, migration and/or invasion of tumorous cells; and/or for treating a glioma, wherein the inhibitor is a compound according to the following:

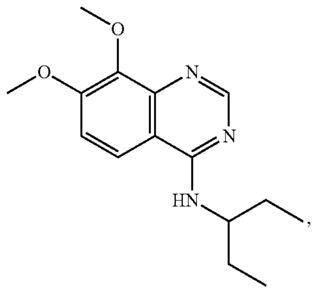

,

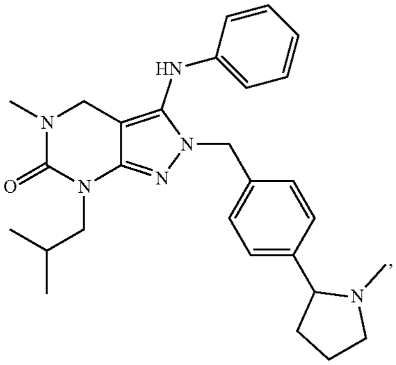

,

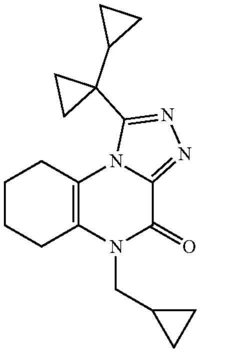

or

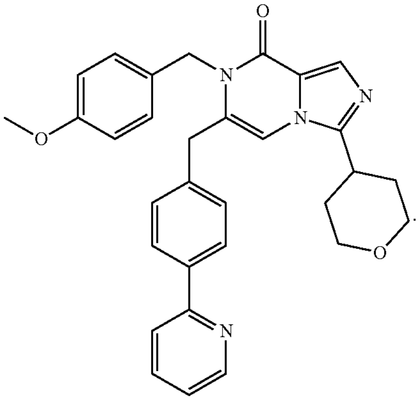

.

Further examples of PDE1 inhibitors suitable for use in the methods and treatments discussed herein can be found in International Publication WO2006133261A2; U.S. Pat. Nos. 8,273,750; 9,000,001; 9,624,230; International Publication WO2009075784A1; U.S. Pat. Nos. 8,273,751; 8,829,008; 9,403,836; International Publication WO2014151409A1, U.S. Pat. Nos. 9,073,936; 9,598,426; 9,556,186; U.S. Publication 2017/0231994A1, International Publication WO2016022893A1, and U.S. Publication 2017/0226117A1, each of which are incorporated by reference in their entirety.

Still further examples of PDE1 inhibitors suitable for use in the methods and treatments discussed herein can be found in International Publication WO2018007249A1; U.S. Publication 2018/0000786; International Publication WO2015118097A1; U.S. Pat. No. 9,718,832; International Publication WO2015091805A1; U.S. Pat. No. 9,701,665; U.S. Publication 2015/0175584A1; U.S. Publication 2017/0267664A1; International Publication WO2016055618A1; U.S. Publication 2017/0298072A1; International Publication WO2016170064A1; U.S. Publication 2016/0311831A1; International Publication WO2015150254A1; U.S. Publication 2017/0022186A1; International Publication WO2016174188A1; U.S. Publication 2016/0318939A1; U.S. Publication 2017/0291903A1; International Publication WO2018073251A1; International Publication WO2017178350A1; and U.S. Publication 2017/0291901A1; each of which are incorporated by reference in their entirety. In any situation in which the statements of any documents incorporated by reference contradict or are incompatible with any statements made in the present disclosure, the statements of the present disclosure shall be understood as controlling.

If not otherwise specified or clear from context, the following terms herein have the following meanings:

(a) "Selective PDE1 inhibitor" as used herein refers to a PDE1 inhibitor with at least 100-fold selectivity for PDE1 inhibition over inhibition of any other PDE isoform.

(b) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

(c) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

(d) "Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

(e) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(f) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

Compounds of the Disclosure, e.g., PDE1 inhibitors as described herein, may exist in free or salt form, e.g., as acid addition salts. In this specification unless otherwise indicated, language such as "Compounds of the Disclosure" is to be understood as embracing the compounds in any form, for example free or acid addition salt form, or where the compounds contain acidic substituents, in base addition salt form. The Compounds of the Disclosure are intended for use as pharmaceuticals, therefore pharmaceutically acceptable salts are preferred. Salts which are unsuitable for pharmaceutical uses may be useful, for example, for the isolation or purification of free Compounds of the Disclosure or their pharmaceutically acceptable salts, are therefore also included.

Compounds of the Disclosure may in some cases also exist in prodrug form. A prodrug form is compound which converts in the body to a Compound of the Disclosure. For example, when the Compounds of the Disclosure contain hydroxy or carboxy substituents, these substituents may form physiologically hydrolysable and acceptable esters. As used herein, "physiologically hydrolysable and acceptable ester" means esters of Compounds of the Disclosure which are hydrolysable under physiological conditions to yield acids (in the case of Compounds of the Disclosure which have hydroxy substituents) or alcohols (in the case of Compounds of the Disclosure which have carboxy substituents) which are themselves physiologically tolerable at doses to be administered. Therefore, wherein the Compound of the Disclosure contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Disclosure contains a carboxylic acid, for example, Compound-C(O)OH, the acid ester prodrug of such compound, Compound-C(O)O—C1-4alkyl can hydrolyze to form Compound-C(O)OH and HO—C1-4alkyl. As will be appreciated the term thus embraces conventional pharmaceutical prodrug forms.

In another embodiment, the disclosure further provides a pharmaceutical composition comprising a PDE1 inhibitor in combination with an antitumor agent, each in free or pharmaceutically acceptable salt form, in admixture with a pharmaceutically acceptable carrier. The term "combination," as used herein, embraces simultaneous, sequential, or contemporaneous administration of the PDE1 inhibitor and the antitumor agent. In another embodiment, the disclosure provides a pharmaceutical composition containing such a compound. In some embodiments, the combination of the PDE1 inhibitor and the antitumor agent allows the antitumor agent to be administered in a dosage lower than would be effective if administered as sole monotherapy.

Methods of Using Compounds of the Disclosure

In another embodiment, the present application provides for a method (Method 1) of treating a condition selected from a cancer or tumor comprising administering a pharmaceutically acceptable amount of a PDE1 inhibitor (i.e., PDE1 inhibitor according to Formula I, Ia, II, III and/or IV) to a subject in need thereof.

1.1 Method 1, wherein the cancer or tumor is characterized by an increased expression of PDE1 relative to normal cells of the same tissue type as the cancerous or tumorous cells.

1.2 Any preceding method, wherein the cancer or tumor is characterized by an increased expression of PDE1C relative to normal cells of the same tissue type as the cancerous or tumorous cells.

1.3 Any of the preceding methods, wherein the cancer cells exhibit one or more of increased PDE1 RNA expression, DNA copy number, PDE1 binding (e.g., PET or radio-isotope retention of PDE1 inhibitor molecules), or PDE1 enzymatic activity (e.g., as measured in an enzymatic assay or as reflected in low levels of CAMP in the cancer cells or subcellular domain, eg microtubule domains, of the cancer cells) relative to normal cells of the same tissue type as the cancer cells.

1.4 Any preceding method, wherein the condition is a tumor.

1.5 Any preceding Method, wherein the tumor is selected from one or more of acoustic neuroma, astrocytoma, chordoma, CNS lymphoma, craniopharyngioma, gliomas (e.g., Brain stem glioma, ependymoma, mixed glioma, optic nerve glioma), subependymoma, medulloblastoma, meningioma, metastatic brain tumors, oligodendroglioma, pituitary tumors, primitive neuroectodermal (PNET), schwannoma, adenomas (e.g., basophilic adenoma, eosinophilic adenoma, chromophobe adenoma, parathyroid adenoma, islet adenoma, fibroadenoma), fibroids (fibrous histiocytoma), fibromas, hemangiomas, lipomas (e.g., angiolipoma, myelolipoma, fibrolipoma, spindle cell lipoma, hibernoma, atypical lipoma), myxoma, osteoma, preleukemias, rhadomyoma, papilloma, seborrheic keratosis, skin adnexal tumors, hepatic adenomas, renal tubular adenoma, bile duct adenoma, transitional cell papilloma, hydatidiform moles, ganglioneuroma, meningoma, neurilemmoma, neurofibroma, C cell hyperplasia, pheochromocytoma, insulinoma, gastrinoma, carcinoids, chemodectoma, paraganglioma, nevus, actinic keratosis, cervical dysplasia, metaplasia (e.g., metaplasia of the lung), leukoplakia, hemangioma, lymphangioma, carcinoma (e.g., squamous cell carcinoma, epidermoid carcinoma, adenocarcinoma, hepatoma, hepatocellular carcinoma, renal cell carcinoma, cholangiocarcinoma, transitional cell carcinoma, embryonal cell carcinoma, parathyroid carcinoma, medullary carcinoma of thyroid, bronchial carcinoid, oat cell carcinoma, islet cell carcinoma, malignant carcinoid), sarcoma (e.g., fibrosarcoma, myxosarcoma, liposarcoma, chondrosarcoma, osteosarcoma, malignant fibrous histiocytoma, hemangiosarcoma, angiosarcoma, lymphangiosarcoma, leiomyosarcoma, rhabdomyosarcoma, neurofibrosarcoma), blastoma (e.g., medulloblastoma and glioblastoma, types of brain tumor, retinoblastoma, a tumor in the retina of the eye, osteoblastoma, bone tumors, neuroblastoma), germ cell tumor, mesothelioma, malignant skin adnexal tumors, hypernephroma, seminoma, glioma, malignant meningioma, malignant shwannoma, malignant pheochromocytoma, malignant paraganglioma, melanoma, mercell cell neoplasm, cystosarcoma phylloides, or Wilms tumor.

1.6 Any preceding method, wherein the condition is a glioma, osteosarcoma, melanoma, leukemia, or neuroblastoma.

1.7 Any preceding method, wherein the condition is a glioma (e.g., ependymoma, astrocytoma, oligodendrogliomas, brain stem glioma, optic nerve glioma, or mixed gliomas, e.g., oligoastrocytomas).

1.8 Method 1.6, wherein the glioma is an astrocytoma (e.g., glioblastoma multiforme).

1.9 Any preceding method, wherein the condition is glioblastoma multiforme.

1.10 Any of Methods 1-1.2, wherein the condition is a cancer.

1.11 Any of Methods 1-1.2 or 1.10, wherein the condition is leukemia.

1.12 Method 1.11, wherein the leukemia is a lymphoctic leukemia or a myelogenous leukemia.

1.13 Any preceding method, further comprising the step of administering an antitumor agent to the patient.

1.14 Method 1.13, wherein the antitumor agent is administered concurrently with the PDE1 inhibitor.

1.15 Method 1.13, wherein the antitumor agent is administered prior to administering the PDE1 inhibitor.

1.16 Method 1.13, wherein the antitumor agent is administered after administering the PDE1 inhibitor.

1.17 Any of the preceding methods, wherein the PDE1 inhibitor, and optionally the antitumor agent, is administered with radiation therapy or chemotherapy.

1.18 Any of the preceding methods, wherein the PDE1 inhibitor, and optionally the antitumor agent, is administered concurrently with radiation therapy or chemotherapy.

1.19 Any of the preceding methods, wherein the PDE1 inhibitor, and optionally the antitumor agent, is administered prior to radiation therapy or chemotherapy.

1.20 Any of the preceding methods, wherein the PDE1 inhibitor, and optionally the antitumor agent, is administered after radiation therapy or chemotherapy.

1.21 Any of the preceding methods, wherein the PDE1 inhibitor is administered together with an antitumor agent, chemotherapeutic, gene therapeutic and/or immunologic treatment.

1.22 Any of the preceding methods, wherein administration of the PDE1 inhibitor is effective to induce one or more of the following in the cancer or tumor cells: apoptotic cell death, inhibition of migration, inhibition of metastasis, and/or reduction of inflammation.

1.23 Any of the preceding methods, wherein the PDE1 inhibitor is administered together with an antitumor agent, chemotherapeutic, gene therapeutic, immunologic treatment, corticosteroid, and/or an antihistamine.

1.24 Any of the preceding methods, wherein the cancer or tumor is mediated by PDE.

1.25 Any of the preceding methods, wherein the cancer or tumor is mediated by PDE1.

1.26 Any of the preceding methods, wherein the cancer or tumor is mediated by PDE1C.

1.27 Any of the preceding methods, wherein the cancer or tumor is characterized by a loss of calcium/calmodulin control.

1.28 Any of the preceding methods, wherein the PDE1 enzymes in the cancerous or tumorous cells have undergone a structural change that alters control of PDE1 activity by calcium/calmodulin.

The disclosure further provides a PDE1 inhibitor for use in a method for the treatment or a condition selected from a cancer or tumor, e.g., for use in any of Methods 1, et seq.

The disclosure further provides the use of a PDE1 inhibitor in the manufacture of a medicament for use in a method of treating of a condition selected from a cancer or tumor, e.g., a medicament for use in any of Methods 1, et seq.

The invention further provides a pharmaceutical composition comprising a PDE1 inhibitor, e.g., any of a Compound of Formula I, Ia, II, III and/or IV, for use in any of Methods 1 et seq.

In another embodiment, the present application provides for a method (Method 2) of inhibiting the proliferation, migration and/or invasion of cancerous or tumorous cells comprising administering a pharmaceutically acceptable amount of a PDE1 inhibitor (i.e., PDE1 inhibitor according to Formula I, Ia, II, III and/or IV) to a subject in need thereof.

2.1 Method 2, wherein the method is for inhibiting the proliferation of cancerous or tumorous cells.

2.2 Any preceding method, wherein the cancerous or tumorous cells are characterized by increased expression of PDE1 relative to normal cells of the same tissue type as the cancerous or tumorous cells.

2.3 Any preceding method, wherein the cancerous or tumorous cells are characterized by increased expression of PDE1C relative to normal cells of the same tissue type as the cancerous or tumorous cells.

2.4 Any of the preceding methods, wherein the cancer cells exhibit one or more of increased PDE1 RNA expression, DNA copy number, PDE1 binding (e.g., PET or radio-isotope retention of PDE1 inhibitor molecules), or PDE1 enzymatic activity (e.g., as measured in an enzymatic assay or as reflected in low levels of CAMP in the cancer cells or subcellular domain, eg microtubule domains, of the cancer cells) relative to normal cells of the same tissue type as the cancer cells.

2.5 Any preceding method, wherein the condition is a tumor.

2.6 Any preceding Method, wherein the tumor is selected from one or more of acoustic neuroma, astrocytoma, chordoma, CNS lymphoma, craniopharyngioma, gliomas (e.g., Brain stem glioma, ependymoma, mixed glioma, optic nerve glioma), subependymoma, medulloblastoma, meningioma, metastatic brain tumors, oligodendroglioma, pituitary tumors, primitive neuroectodermal (PNET), schwannoma, adenomas (e.g., basophilic adenoma, eosinophilic adenoma, chromophobe adenoma, parathyroid adenoma, islet adenoma, fibroadenoma), fibroids (fibrous histiocytoma), fibromas, hemangiomas, lipomas (e.g., angiolipoma, myelolipoma, fibrolipoma, spindle cell lipoma, hibernoma, atypical lipoma), myxoma, osteoma, preleukemias, rhadomyoma, papilloma, seborrheic keratosis, skin adnexal tumors, hepatic adenomas, renal tubular adenoma, bile duct adenoma, transitional cell papilloma, hydatidiform moles, ganglioneuroma, meningoma, neurilemmoma, neurofibroma, C cell hyperplasia, pheochromocytoma, insulinoma, gastrinoma, carcinoids, chemodectoma, paraganglioma, nevus, actinic keratosis, cervical dysplasia, metaplasia (e.g., metaplasia of the lung), leukoplakia, hemangioma, lymphangioma, carcinoma (e.g., squamous cell carcinoma, epidermoid carcinoma, adenocarcinoma, hepatoma, hepatocellular carcinoma, renal cell carcinoma, cholangiocarcinoma, transitional cell carcinoma, embryonal cell carcinoma, parathyroid carcinoma, medullary carcinoma of thyroid, bronchial carcinoid, oat cell carcinoma, islet cell carcinoma, malignant carcinoid), sarcoma (e.g., fibrosarcoma, myxosarcoma, liposarcoma, chondrosarcoma, osteosarcoma, malignant fibrous histiocytoma, hemangiosarcoma, angiosarcoma, lymphangiosarcoma, leiomyosarcoma, rhabdomyosarcoma, neurofibrosarcoma), blastoma (e.g., medulloblastoma and glioblastoma, types of brain tumor, retinoblastoma, a tumor in the retina of the eye, osteoblastoma, bone tumors, neuroblastoma), germ cell tumor, mesothelioma, malignant skin adnexal tumors, hypernephroma, seminoma, glioma, malignant meningioma, malignant shwannoma, malignant pheochromocytoma, malignant paraganglioma, melanoma, mercell cell neoplasm, cystosarcoma phylloides, or Wilms tumor.

2.7 Any preceding method, wherein the condition is a glioma, osteosarcoma, melanoma, leukemia, or neuroblastoma.

2.8 Any preceding method, wherein the condition is a glioma (e.g., ependymoma, astrocytoma, oligodendrogliomas, brain stem glioma, optic nerve glioma, or mixed gliomas, e.g., oligoastrocytomas).

2.9 Method 2.5, wherein the glioma is an astrocytoma (e.g., glioblastoma multiforme).

2.10 Any preceding method, wherein the condition is glioblastoma multiforme.

2.11 Any of Methods 2-2.3, wherein the condition is a cancer.

2.12 Any of Methods 2-2.3 or 2.11, wherein the condition is leukemia.

2.13 Method 2.11, wherein the leukemia is a lymphoctic leukemia or a myelogenous leukemia.

2.14 Any preceding method, further comprising the step of administering an antitumor agent to the patient.

2.15 Method 2.14, wherein the antitumor agent is administered concurrently with the PDE1 inhibitor.

2.16 Method 2.14, wherein the antitumor agent is administered prior to administering the PDE1 inhibitor.

2.17 Method 2.14, wherein the antitumor agent is administered after administering the PDE1 inhibitor.

2.18 Any of the preceding methods, wherein the PDE1 inhitor, and optionally the antitumor agent, is administered with radiation therapy or chemotherapy.

2.19 Any of the preceding methods, wherein the PDE1 inhitor, and optionally the antitumor agent, is administered concurrently with radiation therapy or chemotherapy.

2.20 Any of the preceding methods, wherein the PDE1 inhitor, and optionally the antitumor agent, is administered prior to radiation therapy or chemotherapy.

2.21 Any of the preceding methods, wherein the PDE1 inhitor, and optionally the antitumor agent, is administered after radiation therapy or chemotherapy.

2.22 Any of the preceding methods, wherein the PDE1 inhibitor is administered together with an antitumor agent, chemotherapeutic, gene therapeutic and/or immunologic treatment.

2.23 Any of the preceding methods, wherein the PDE1 inhibitor is administered together with an antitumor agent, chemotherapeutic, gene therapeutic, immunologic treatment, corticosteroid, and/or an antihistamine.

2.24 Any of the preceding methods, wherein the cancer or tumor is mediated by PDE.

2.25 Any of the preceding methods, wherein the cancer or tumor is mediated by PDE1.

2.26 Any of the preceding methods, wherein the cancer or tumor is mediated by PDE1C.

2.27 Any of the preceding methods, wherein the cancer or tumor is characterized by a loss of calcium/calmodulin control.

2.28 Any of the preceding methods, wherein the PDE1 enzymes in the cancerous or tumorous cells have undergone a structural change that alters control of PDE1 activity by calcium/calmodulin.

2.29 Any of the preceding methods, further including the step of assessing a subject's degree of calcium/calmodulin sensitivity in expressed PDE1, restoration of cyclic nucleotide levels, RNA expression of PDE1 or mutation of a PDE1 gene.

The disclosure further provides a PDE1 inhibitor for use in a method for inhibiting the proliferation, migration and/or invasion of cancerous or tumorous cells, e.g., for use in any of Methods 2, et seq.

The disclosure further provides the use of a PDE1 inhibitor in the manufacture of a medicament for use in a method of inhibiting the proliferation, migration and/or invasion of cancerous or tumorous cells, e.g., a medicament for use in any of Methods 2, et seq.

The invention further provides a pharmaceutical composition comprising a PDE1 inhibitor, e.g., any of a Compound of Formula I, Ia, II, III and/or IV, for use in any of Methods 2, et seq.

In another embodiment, the present application provides for a method (Method 3) of treating a glioma comprising administering a pharmaceutically acceptable amount of a PDE1 inhibitor (i.e., PDE1 inhibitor according to Formula I, Ia, II, III and/or IV) to a subject in need thereof.

3.1 Method 3, wherein the glioma is characterized by an increased expression of PDE1 relative to normal cells of the same tissue type as the affected glial cells.

3.2 Any preceding method, wherein the glioma is characterized by an increased expression of PDE1C relative to normal cells of the same tissue type as the affected glial cells.

3.3 Any of the preceding methods, wherein the glioma is characterized by one or more of increased PDE1 RNA expression, DNA copy number, PDE1 binding (e.g., PET or radio-isotope retention of PDE1 inhibitor molecules), or PDE1 enzymatic activity (e.g., as measured in an enzymatic assay or as reflected in low levels of CAMP in the cancer cells or subcellular domain, eg microtubule domains, of the cancer cells) relative to normal cells of the same tissue type as the cancer cells.

3.4 Any preceding method, wherein the glioma is an astrocytoma (e.g., glioblastoma multiforme).

3.5 Any preceding method, wherein the condition is glioblastoma multiforme.

3.6 Any preceding method, further comprising the step of administering an antitumor agent to the patient.

3.7 Method 3.6, wherein the antitumor agent is administered concurrently with the PDE1 inhibitor.

3.8 Method 3.6, wherein the antitumor agent is administered prior to administering the PDE1 inhibitor.

3.9 Method 3.6, wherein the antitumor agent is administered after administering the PDE1 inhibitor.

3.10 Any of the preceding methods, wherein the PDE1 inhibitor, and optionally the antitumor agent, is administered with radiation therapy or chemotherapy.

3.11 Any of the preceding methods, wherein the PDE1 inhitor, and optionally the antitumor agent, is administered concurrently with radiation therapy or chemotherapy.

3.12 Any of the preceding methods, wherein the PDE1 inhitor, and optionally the antitumor agent, is administered prior to radiation therapy or chemotherapy.

3.13 Any of the preceding methods, wherein the PDE1 inhitor, and optionally the antitumor agent, is administered after radiation therapy or chemotherapy.

3.14 Any of the preceding methods, wherein the PDE1 inhibitor is administered together with an antitumor agent, chemotherapeutic, gene therapeutic and/or immunologic treatment.

3.15 Any of the preceding methods, wherein administration of the PDE1 inhibitor is effective to induce one or more of the following in the glioma: apoptotic cell death, inhibition of migration, inhibition of metastasis, and/or reduction of inflammation.

3.16 Any of the preceding methods, wherein the PDE1 inhibitor is administered together with an antitumor agent, chemotherapeutic, gene therapeutic, immunologic treatment, corticosteroid, and/or an antihistamine.

3.17 Any of the preceding methods, wherein the glioma is mediated by PDE.

3.18 Any of the preceding methods, wherein the glioma is mediated by PDE1.

3.19 Any of the preceding methods, wherein the glioma is mediated by PDE1C.

3.20 Any of the preceding methods, wherein the glioma is characterized by a loss of calcium/calmodulin control.

3.21 Any of the preceding methods, wherein the PDE1 enzymes in the glioma cells have undergone a structural change that alters control of PDE1 activity by calcium/calmodulin.

The disclosure further provides a PDE1 inhibitor for use in a method for treating a glioma, e.g., for use in any of Methods 3, et seq.

The disclosure further provides the use of a PDE1 inhibitor in the manufacture of a medicament for use in a method of treating a glioma, e.g., a medicament for use in any of Methods 3, et seq.

The invention further provides a pharmaceutical composition comprising a PDE1 inhibitor, e.g., any of a Compound of Formula I, Ia, II, III and/or IV, for use in any of Methods 4, et seq.

In another embodiment, the present application provides for a method (Method 4) of treating a cancer in a patient wherein the cancer cells have elevated PDE1 activity or expression, e.g. wherein the cancer cells exhibit one or more of increased PDE1 RNA expression, DNA copy number, PDE1 binding (e.g., PET or radio-isotope retention of PDE1 inhibitor molecules), or PDE1 enzymatic activity (e.g., as measured in an enzymatic assay or as reflected in low levels of CAMP in the cancer cells or subcellular domain, eg microtubule domains, of the cancer cells) relative to normal cells of the same tissue type as the cancer cells, comprising administering to the patient an effective amount of a PDE1 inhibitor (i.e., PDE1 inhibitor according to Formula I, Ia, II, III and/or IV) alone or in combination with chemotherapeutics, gene therapeutics and/or immunologic treatments to a subject in need thereof.

4.1 Method 4, wherein the method is for inhibiting the proliferation of cancerous or tumorous cells.

4.2 Any preceding method, wherein the cancerous or tumorous cells are characterized by increased expression or activity of PDE1 relative to normal cells of the same tissue type as the cancerous or tumorous cells.

4.3 Any preceding method, wherein the cancerous or tumorous cells are characterized by increased expression of PDE1C relative to normal cells of the same tissue type as the cancerous or tumorous cells.

4.4 Any of the preceding methods, wherein the cancer cells exhibit one or more of increased PDE1 RNA expression, DNA copy number, PDE1 binding (e.g., PET or radio-isotope retention of PDE1 inhibitor molecules), or PDE1 enzymatic activity (e.g., as measured in an enzymatic assay or as reflected in low levels of CAMP in the cancer cells or subcellular domain, eg microtubule domains, of the cancer cells) relative to normal cells of the same tissue type as the cancer cells.

4.5 Any preceding method, wherein the condition is a tumor.

4.6 Any preceding Method, wherein the tumor is selected from one or more of acoustic neuroma, astrocytoma, chordoma, CNS lymphoma, craniopharyngioma, gliomas (e.g., Brain stem glioma, ependymoma, mixed glioma, optic nerve glioma), subependymoma, medulloblastoma, meningioma, metastatic brain tumors, oligodendroglioma, pituitary tumors, primitive neuroectodermal (PNET), schwannoma, adenomas (e.g., basophilic adenoma, eosinophilic adenoma, chromophobe adenoma, parathyroid adenoma, islet adenoma, fibroadenoma), fibroids (fibrous histiocytoma), fibromas, hemangiomas, lipomas (e.g., angiolipoma, myelolipoma, fibrolipoma, spindle cell lipoma, hibernoma, atypical lipoma), myxoma, osteoma, preleukemias, rhadomyoma, papilloma, seborrheic keratosis, skin adnexal tumors, hepatic adenomas, renal tubular adenoma, bile duct adenoma, transitional cell papilloma, hydatidiform moles, ganglioneuroma, meningoma, neurilemmoma, neurofibroma, C cell hyperplasia, pheochromocytoma, insulinoma, gastrinoma, carcinoids, chemodectoma, paraganglioma, nevus, actinic keratosis, cervical dysplasia, metaplasia (e.g., metaplasia of the lung), leukoplakia, hemangioma, lymphangioma, carcinoma (e.g., squamous cell carcinoma, epidermoid carcinoma, adenocarcinoma, hepatoma, hepatocellular carcinoma, renal cell carcinoma, cholangiocarcinoma, transitional cell carcinoma, embryonal cell carcinoma, parathyroid carcinoma, medullary carcinoma of thyroid, bronchial carcinoid, oat cell carcinoma, islet cell carcinoma, malignant carcinoid), sarcoma (e.g., fibrosarcoma, myxosarcoma, liposarcoma, chondrosarcoma, osteosarcoma, malignant fibrous histiocytoma, hemangiosarcoma, angiosarcoma, lymphangiosarcoma, leiomyosarcoma, rhabdomyosarcoma, neurofibrosarcoma), blastoma (e.g., medulloblastoma and glioblastoma, types of brain tumor, retinoblastoma, a tumor in the retina of the eye, osteoblastoma, bone tumors, neuroblastoma), germ cell tumor, mesothelioma, malignant skin adnexal tumors, hypernephroma, seminoma, glioma, malignant meningioma, malignant shwannoma, malignant pheochromocytoma, malignant paraganglioma, melanoma, mercell cell neoplasm, cystosarcoma phylloides, or Wilms tumor.

4.7 Any preceding method, wherein the condition is a glioma, osteosarcoma, melanoma, leukemia, or neuroblastoma.

4.8 Any preceding method, wherein the condition is a glioma (e.g., ependymoma, astrocytoma, oligodendrogliomas, brain stem glioma, optic nerve glioma, or mixed gliomas, e.g., oligoastrocytomas).

4.9 Method 4.8, wherein the glioma is an astrocytoma (e.g., glioblastoma multiforme).

4.10 Any preceding method, wherein the condition is glioblastoma multiforme.

4.11 Any of Methods 4-4.3, wherein the condition is a cancer.

4.12 Any of Methods 4-4.3 or 4.11, wherein the condition is leukemia.

4.13 Method 4.12, wherein the leukemia is a lymphoctic leukemia or a myelogenous leukemia.

4.14 Any preceding method, further comprising the step of administering an antitumor agent to the patient.

4.15 Method 4.14, wherein the antitumor agent is administered concurrently with the PDE1 inhibitor.

4.16 Method 4.14, wherein the antitumor agent is administered prior to administering the PDE1 inhibitor.

4.17 Method 4.14, wherein the antitumor agent is administered after administering the PDE1 inhibitor.

4.18 Any of the preceding methods, wherein the PDE1 inhitor, and optionally the antitumor agent, is administered with radiation therapy or chemotherapy.

4.19 Any of the preceding methods, wherein the PDE1 inhitor, and optionally the antitumor agent, is administered concurrently with radiation therapy or chemotherapy.

4.20 Any of the preceding methods, wherein the PDE1 inhitor, and optionally the antitumor agent, is administered prior to radiation therapy or chemotherapy.

4.21 Any of the preceding methods, wherein the PDE1 inhitor, and optionally the antitumor agent, is administered after radiation therapy or chemotherapy.

4.22 Any of the preceding methods, wherein administration of the PDE1 inhibitor is effective to induce one or more of the following in the cancer cells: apoptotic cell death, inhibition of migration, inhibition of metastasis, and/or reduction of inflammation.

4.23 Any of the preceding methods, wherein the PDE1 inhibitor is administered together with an antitumor agent, chemotherapeutic, gene therapeutic, immunologic treatment, corticosteroid, and/or an antihistamine.

4.24 Any of the preceding methods, wherein the cancer or tumor is mediated by PDE.

4.25 Any of the preceding methods, wherein the cancer or tumor is mediated by PDE1.

4.26 Any of the preceding methods, wherein the cancer or tumor is mediated by PDE1C.

4.27 Any of the preceding methods, wherein the cancer is characterized by a loss of calcium/calmodulin control.

4.28 Any of the preceding methods, wherein the PDE1 enzymes in the cancer cells have undergone a structural change that alters control of PDE1 activity by calcium/calmodulin.

The disclosure further provides a PDE1 inhibitor for use in a method of treating a cancer in a patient wherein the cancer cells have elevated PDE1 activity or expression, e.g. wherein the cancer cells exhibit one or more of increased PDE1 RNA expression, DNA copy number, PDE1 binding (e.g., PET or radio-isotope retention of PDE1 inhibitor molecules), or PDE1 enzymatic activity (e.g., as measured in an enzymatic assay or as reflected in low levels of CAMP in the cancer cells or subcellular domain, eg microtubule domains, of the cancer cells) relative to normal cells of the same tissue type as the cancer cells, e.g., for use in any of Methods 4, et seq.

The disclosure further provides the use of a PDE1 inhibitor in the manufacture of a medicament for use in a method of treating a cancer in a patient wherein the cancer cells have elevated PDE1 activity or expression, e.g. wherein the cancer cells exhibit one or more of increased PDE1 RNA expression, DNA copy number, PDE1 binding (e.g., PET or radio-isotope retention of PDE1 inhibitor molecules), loss of calcium/calmodulin control the enzyme becomes constitutively active or PDE1 enzymatic activity (e.g., as measured in an enzymatic assay or as reflected in low levels of CAMP in the cancer cells or subcellular domain, eg microtubule domains, of the cancer cells) relative to normal cells of the same tissue type as the cancer cells, e.g., a medicament for use in any of Methods 4, et seq.

The invention further provides a pharmaceutical composition comprising a PDE1 inhibitor, e.g., any of a Compound of Formula I, Ia, II, III and/or IV, for use in any of Methods 4, et seq.

In another embodiment, the present application provides for a method (Method 5) of inhibiting cytokine release syndrome, comprising administering an effective amount of a PDE1 inhibitor to a patient in need thereof, e.g. wherein the patient is suffering from cancer and is receiving one or more of chemotherapeutic treatment, immunologic treatment, gene therapy and/or antibody therapy (including antibodies directed to cancer antigens and/or antibodies to immune checkpoint targets), and wherein the method optionally further comprises administration of corticosteroids and/antihistamines to the patient.

5.1 Method 5, wherein the wherein the patient is suffering from cancer.

5.2 Any preceding method, wherein the cancerous or tumorous cells are characterized by increased expression or activity of PDE1 relative to normal cells of the same tissue type as the cancerous or tumorous cells.

5.3 Any preceding method, wherein the cancerous or tumorous cells are characterized by increased expression of PDE1C relative to normal cells of the same tissue type as the cancerous or tumorous cells.

5.4 Any of methods 5.1-5.3, wherein the cancer cells exhibit one or more of increased PDE1 RNA expression, DNA copy number, PDE1 binding (e.g., PET or radio-isotope retention of PDE1 inhibitor molecules), or PDE1 enzymatic activity (e.g., as measured in an enzymatic assay or as reflected in low levels of cAMP in the cancer cells or subcellular domain, eg microtubule domains, of the cancer cells) relative to normal cells of the same tissue type as the cancer cells.

5.5 Any preceding method, wherein the patient is suffering from a tumor.

5.6 Any preceding method, wherein the patient is suffering from a tumor selected from one or more of acoustic neuroma, astrocytoma, chordoma, CNS lymphoma, craniopharyngioma, gliomas (e.g., Brain stem glioma, ependymoma, mixed glioma, optic nerve glioma), subependymoma, medulloblastoma, meningioma, metastatic brain tumors, oligodendroglioma, pituitary tumors, primitive neuroectodermal (PNET), schwannoma, adenomas (e.g., basophilic adenoma, eosinophilic adenoma, chromophobe adenoma, parathyroid adenoma, islet adenoma, fibroadenoma), fibroids (fibrous histiocytoma), fibromas, hemangiomas, lipomas (e.g., angiolipoma, myelolipoma, fibrolipoma, spindle cell lipoma, hibernoma, atypical lipoma), myxoma, osteoma, preleukemias, rhadomyoma, papilloma, seborrheic keratosis, skin adnexal tumors, hepatic adenomas, renal tubular adenoma, bile duct adenoma, transitional cell papilloma, hydatidiform moles, ganglioneuroma, meningoma, neurilemmoma, neurofibroma, C cell hyperplasia, pheochromocytoma, insulinoma, gastrinoma, carcinoids, chemodectoma, paraganglioma, nevus, actinic keratosis, cervical dysplasia, metaplasia (e.g., metaplasia of the lung), leukoplakia, hemangioma, lymphangioma, carcinoma (e.g., squamous cell carcinoma, epidermoid carcinoma, adenocarcinoma, hepatoma, hepatocellular carcinoma, renal cell carcinoma, cholangiocarcinoma, transitional cell carcinoma, embryonal cell carcinoma, parathyroid carcinoma, medullary carcinoma of thyroid, bronchial carcinoid, oat cell carcinoma, islet cell carcinoma, malignant carcinoid), sarcoma (e.g., fibrosarcoma, myxosarcoma, liposarcoma, chondrosarcoma, osteosarcoma, malignant fibrous histiocytoma, hemangiosarcoma, angiosarcoma, lymphangiosarcoma, leiomyosarcoma, rhabdomyosarcoma, neurofibrosarcoma), blastoma (e.g., medulloblastoma and glioblastoma, types of brain tumor, retinoblastoma, a tumor in the retina of the eye, osteoblastoma, bone tumors, neuroblastoma), germ cell tumor, mesothelioma, malignant skin adnexal tumors, hypernephroma, seminoma, glioma, malignant meningioma, malignant shwannoma, malignant pheochromocytoma, malignant paraganglioma, melanoma, mercell cell neoplasm, cystosarcoma phylloides, or Wilms tumor.

5.7 Any preceding method, wherein the patient is suffering from a glioma, osteosarcoma, melanoma, leukemia, or neuroblastoma.

5.8 Any preceding method, wherein the patient is suffering from a glioma (e.g., ependymoma, astrocytoma, oligodendrogliomas, brain stem glioma, optic nerve glioma, or mixed gliomas, e.g., oligoastrocytomas).

5.9 Method 5.8, wherein the patient is suffering from an astrocytoma (e.g., glioblastoma multiforme).

5.10 Any preceding method, wherein the patient is suffering from glioblastoma multiforme.

5.11 Any preceding method, wherein the patient is suffering from cancer.

5.12 Any preceding method, wherein the patient is suffering from leukemia.

5.13 Method 5.12, wherein the leukemia is a lymphoctic leukemia or a myelogenous leukemia.

5.14 Any preceding method, further comprising the step of administering an antitumor agent to the patient.

5.15 Method 5.14, wherein the antitumor agent is administered concurrently with the PDE1 inhibitor.

5.16 Method 5.14, wherein the antitumor agent is administered prior to administering the PDE1 inhibitor.

5.17 Method 5.14, wherein the antitumor agent is administered after administering the PDE1 inhibitor.

5.18 Any of the preceding methods, wherein the PDE1 inhitor, and optionally the antitumor agent, is administered with radiation therapy or chemotherapy.

5.19 Any of the preceding methods, wherein the PDE1 inhitor, and optionally the antitumor agent, is administered concurrently with radiation therapy or chemotherapy.

5.20 Any of the preceding methods, wherein the PDE1 inhitor, and optionally the antitumor agent, is administered prior to radiation therapy or chemotherapy.

5.21 Any of the preceding methods, wherein the PDE1 inhitor, and optionally the antitumor agent, is administered after radiation therapy or chemotherapy.

5.22 Any of the preceding methods, wherein Foregoing method wherein administration of the PDE1 inhibitor is effective to induce one or more of the following in the cancer cells: apoptotic cell death, inhibition of migration, inhibition of metastasis, and/or reduction of inflammation.

5.23 Any of the preceding methods, wherein the PDE1 inhibitor is administered together with an antitumor agent, chemotherapeutic, gene therapeutic, immunologic treatment corticosteroid, and/or an antihistamine.

5.24 Any of Methods 5.1-5.23, wherein the cancer or tumor is mediated by PDE.

5.25 Any of Methods 5.1-5.24, wherein the cancer or tumor is mediated by PDE1.

5.26 Any of Methods 5.1-5.25, wherein the cancer or tumor is mediated by PDE1C.

5.27 Any of Methods 5.1-5.26, wherein the cancer or tumor is characterized by a loss of calcium/calmodulin control.

5.28 Any of Methods 5.1-5.26, wherein the PDE1 enzymes in the cancerous or tumorous cells have undergone a structural change that alters control of PDE1 activity by calcium/calmodulin.

The disclosure further provides a PDE1 inhibitor for use in a method of inhibiting cytokine release syndrome, e.g., for use in any of Methods 5, et seq.

The disclosure further provides the use of a PDE1 inhibitor in the manufacture of a medicament for use in a method of inhibiting cytokine release syndrome, e.g., a medicament for use in any of Methods 5, et seq.

The invention further provides a pharmaceutical composition comprising a PDE1 inhibitor, e.g., any of a Compound of Formula I, Ia, II, III and/or IV, for use in any of Methods 5, et seq.

In another embodiment, the present application provides a method (Method 6) of treating a cancer or tumor characterized by constitutively active PDE1, the method comprising administering an effective amount of a PDE1 inhibitor (i.e., PDE1 inhibitor according to Formula I, Ia, II, III and/or IV) to a patient in need thereof.

6.1 Method 6, wherein the PDE1 in the cancer or tumor cells has become independent of Ca2+/calmodulin mediation.

6.2 Method 6 or 6.1, wherein the PDE1 is PDE1A.

6.3 Method 6 or 6.1, wherein the PDE1 is PDE1B.

6.4 Method 6 or 6.1, wherein the PDE1 is PDE1C.

6.5 Any preceding method, wherein the cancer or tumor is characterized by an increased expression of PDE1 relative to normal cells of the same tissue type as the cancerous or tumorous cells.

6.6 Any preceding method, wherein the cancer or tumor is characterized by an increased expression of PDE1C relative to normal cells of the same tissue type as the cancerous or tumorous cells.

6.7 Any of the preceding methods, wherein the cancer or tumor is characterized by one or more of increased PDE1 RNA expression, DNA copy number, PDE1 binding (e.g., PET or radio-isotope retention of PDE1 inhibitor molecules), or PDE1 enzymatic activity (e.g., as measured in an enzymatic assay or as reflected in low levels of CAMP in the cancer cells or subcellular domain, eg microtubule domains, of the cancer cells) relative to normal cells of the same tissue type as the cancer cells.

6.8 Any preceding method, wherein the condition is a tumor.

6.9 Any preceding Method, wherein the tumor is selected from one or more of acoustic neuroma, astrocytoma, chordoma, CNS lymphoma, craniopharyngioma, gliomas (e.g., Brain stem glioma, ependymoma, mixed glioma, optic nerve glioma), subependymoma, medulloblastoma, meningioma, metastatic brain tumors, oligodendroglioma, pituitary tumors, primitive neuroectodermal (PNET), schwannoma, adenomas (e.g., basophilic adenoma, eosinophilic adenoma, chromophobe adenoma, parathyroid adenoma, islet adenoma, fibroadenoma), fibroids (fibrous histiocytoma), fibromas, hemangiomas, lipomas (e.g., angiolipoma, myelolipoma, fibrolipoma, spindle cell lipoma, hibernoma, atypical lipoma), myxoma, osteoma, preleukemias, rhadomyoma, papilloma, seborrheic keratosis, skin adnexal tumors, hepatic adenomas, renal tubular adenoma, bile duct adenoma, transitional cell papilloma, hydatidiform moles, ganglioneuroma, meningoma, neurilemmoma, neurofibroma, C cell hyperplasia, pheochromocytoma, insulinoma, gastrinoma, carcinoids, chemodectoma, paraganglioma, nevus, actinic keratosis, cervical dysplasia, metaplasia (e.g., metaplasia of the lung), leukoplakia, hemangioma, lymphangioma, carcinoma (e.g., squamous cell carcinoma, epidermoid carcinoma, adenocarcinoma, hepatoma, hepatocellular carcinoma, renal cell carcinoma, cholangiocarcinoma, transitional cell carcinoma, embryonal cell carcinoma, parathyroid carcinoma, medullary carcinoma of thyroid, bronchial carcinoid, oat cell carcinoma, islet cell carcinoma, malignant carcinoid), sarcoma (e.g., fibrosarcoma, myxosarcoma, liposarcoma, chondrosarcoma, osteosarcoma, malignant fibrous histiocytoma, hemangiosarcoma, angiosarcoma, lymphangiosarcoma, leiomyosarcoma, rhabdomyosarcoma, neurofibrosarcoma), blastoma (e.g., medulloblastoma and glioblastoma, types of brain tumor, retinoblastoma, a tumor in the retina of the eye, osteoblastoma, bone tumors, neuroblastoma), germ cell tumor, mesothelioma, malignant skin adnexal tumors, hypernephroma, seminoma, glioma, malignant meningioma, malignant shwannoma, malignant pheochromocytoma, malignant paraganglioma, melanoma, mercell cell neoplasm, cystosarcoma phylloides, or Wilms tumor.

6.10 Any preceding method, wherein the condition is a glioma, osteosarcoma, melanoma, leukemia, or neuroblastoma.

6.11 Any preceding method, wherein the condition is a glioma (e.g., ependymoma, astrocytoma, oligodendrogliomas, brain stem glioma, optic nerve glioma, or mixed gliomas, e.g., oligoastrocytomas).

6.12 The preceding method, wherein the glioma is an astrocytoma (e.g., glioblastoma multiforme).

6.13 Any preceding method, wherein the condition is glioblastoma multiforme.

6.14 Any preceding method, wherein the condition is glioblastoma multiforme characterized by the presence of constitutively active PDE1 (e.g., PDE1C).

6.15 Any of Methods 6-6.7, wherein the condition is a cancer.

6.16 Any of Methods 6-6.7 or 6.15, wherein the condition is leukemia.

6.17 The preceding method, wherein the leukemia is a lymphoctic leukemia or a myelogenous leukemia.

6.18 Any preceding method, further comprising the step of administering an antitumor agent to the patient.

6.19 Method 6.18, wherein the antitumor agent is administered concurrently with the PDE1 inhibitor.

6.20 Method 6.18, wherein the antitumor agent is administered prior to administering the PDE1 inhibitor.

6.21 Method 6.18, wherein the antitumor agent is administered after administering the PDE1 inhibitor.

6.22 Any of the preceding methods, wherein the PDE1 inhitor, and optionally the antitumor agent, is administered with radiation therapy or chemotherapy.

6.23 Any of the preceding methods, wherein the PDE1 inhitor, and optionally the antitumor agent, is administered concurrently with radiation therapy or chemotherapy.

6.24 Any of the preceding methods, wherein the PDE1 inhitor, and optionally the antitumor agent, is administered prior to radiation therapy or chemotherapy.

6.25 Any of the preceding methods, wherein the PDE1 inhitor, and optionally the antitumor agent, is administered after radiation therapy or chemotherapy.

6.26 Any of the preceding methods, wherein the PDE1 inhibitor is administered together with an antitumor agent, chemotherapeutic, gene therapeutic and/or immunologic treatment.

6.27 Any of the preceding methods, wherein the cancer or tumor is mediated by PDE.

6.28 Any of the preceding methods, wherein the cancer or tumor is mediated by PDE1.

6.29 Any of the preceding methods, wherein the cancer or tumor is mediated by PDE1C.

6.30 Any of the preceding methods, wherein the cancer or tumor is characterized by a loss of calcium/calmodulin control.

6.31 Any of the preceding methods, wherein the PDE1 enzymes in the cancerous or tumorous cells have undergone a structural change that alters control of PDE1 activity by calcium/calmodulin.

The disclosure further provides a PDE1 inhibitor for use in a method of treating a cancer or tumor characterized by constitutively active PDE1, e.g., for use in any of Methods 6, et seq.

The disclosure further provides the use of a PDE1 inhibitor in the manufacture of a medicament for use in a method of treating a cancer or tumor characterized by constitutively active PDE1, e.g., a medicament for use in any of Methods 6, et seq.

The invention further provides a pharmaceutical composition comprising a PDE1 inhibitor, e.g., any of a Compound of Formula I, Ia, II, III and/or IV, for use in any of Methods 6, et seq.

In some embodiments, the pharmaceutical compositions are administered in combination with one or more antitumor drugs, for example, drugs known to have an effect in treating or eliminating various types of cancers and/or tumors. Non-limiting examples of antitumor drugs are Abemaciclib, Abiraterone Acetate, Abitrexate (Methotrexate), Abraxane (Paclitaxel Albumin-stabilized Nanoparticle Formulation), ABVD, ABVE, ABVE-PC, AC, Acalabrutinib, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tabets (Melphalan), Aloxi (Palonosetron Hydrochloride), Alunbrig (Brigatinib), Ambochlorin (Chlorambucil), Amboclorin (Chlorambucil), Amifostine, Aminolevulinic Acid, Anastrozole, Aprepitant, Aredia, Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axicabtagene Ciloleucel, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Calquence (Acalabrutinib), Campath (Alemtuzumab), Camptosar (Irinotecan Hydrochloride), Capecitabine, CAPOX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil-Topical, Flutamide, Folex (Methotrexate), Folex PFS (Methotrexate), Folfiri, Folfiri-Bevacizumab, Folfiri-Cetuximab, Folfirinox, Folfox, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, Gemcitabine-Cisplatin, Gemcitabine-Oxaliplatin, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspagase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Valrubicin, Valstar (Valrubicin), Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yescarta (Axicabtagene Ciloleucel), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), Zytiga (Abiraterone Acetate).

As used herein, the term "antitumor agent" is understood to refer to any chemical agents or drugs effective in preventing or inhibiting the formation or growth of cancers or tumors. Antitumor agents as discussed herein may encompass alkylating agents, antimetabolites, natural products, hormones, and/or antibodies. Treatment of tumors or cancer may include limiting the proliferation, migration and/or invasion of cancerous or tumorous cells in the body, or limiting the symptoms associated with said cancer or tumor. As used herein, antitumor agents are understood to encompass and otherwise be synonymous with anticancer agents.

Methods of Making Compounds of the Disclosure

The PDE1 inhibitors of the Disclosure and their pharmaceutically acceptable salts may be made using the methods as described and exemplified in U.S. Pat. No. 8,273,750, US 2006/0173878, U.S. Pat. No. 8,273,751, US 2010/0273753, U.S. Pat. Nos. 8,697,710, 8,664,207, 8,633,180, 8,536,159, US 2012/0136013, US 2011/0281832, US 2013/0085123, US 2013/0324565, US 2013/0338124, US 2013/0331363, WO 2012/171016, and WO 2013/192556, and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds.

Various PDE1 inhibitors and starting materials therefor may be prepared using methods described in US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138. All references cited herein are hereby incorporated by reference in their entirety.

Further PDE1 inhibitors and related methods are disclosed in U.S. Provisional Application 62/833,481, which is hereby incorporated by reference in its entirety. Additional related PDE1 inhibitors and related methods are disclosed in International Publication WO2018/049417, which is hereby incorporated by reference in its entirety.

The Compounds of the Disclosure include their enantiomers, diastereomers and racemates, as well as their polymorphs, hydrates, solvates and complexes. Some individual compounds within the scope of this disclosure may contain double bonds. Representations of double bonds in this disclosure are meant to include both the E and the Z isomer of the double bond. In addition, some compounds within the scope of this disclosure may contain one or more asymmetric centers. This disclosure includes the use of any of the optically pure stereoisomers as well as any combination of stereoisomers.

It is also intended that the Compounds of the Disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Disclosure may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the disclosure is the $^{11}C$ isotope. These radio isotopes are useful for radio-imaging and/or pharmacokinetic studies of the compounds of the disclosure.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

The words "treatment" and "treating" are to be understood accordingly as embracing treatment or amelioration of symptoms of disease as well as treatment of the cause of the disease.

For methods of treatment, the word "effective amount" is intended to encompass a therapeutically effective amount to treat a specific disease or disorder.

The term "patient" include human or non-human (i.e., animal) patient. In particular embodiment, the disclosure encompasses both human and nonhuman. In another embodiment, the disclosure encompasses nonhuman. In other embodiment, the term encompasses human.

The term "comprising" as used in this disclosure is intended to be open-ended and does not exclude additional, un-recited elements or method steps.

Dosages employed in practicing the present disclosure will of course vary depending, e.g. on the particular disease or condition to be treated, the particular Compounds of the Disclosure used, the mode of administration, and the therapy desired. Compounds of the Disclosure may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration of both the PDE1 inhibitor will accordingly be in the range of from about 0.50 to 300 mg, conveniently administered once, or in divided doses 2 to 4 times, daily or in sustained release form. Unit dosage forms for oral administration thus for example may comprise from about 0.2 to 150 or 300 mg, e.g. from about 0.2 or 2.0 to 10, 25, 50, 75 100, 150, or 200 mg of a Compound of the Disclosure, together with a pharmaceutically acceptable diluent or carrier therefor.

Compounds of the Disclosure, particularly for use or administration in any of Methods 1-6, et seq., may be administered at higher doses as necessary to treat a cancer or tumor, e.g., glioblastoma multiforme. It is envisioned that administration of a PDE1 inhibitor for such a method may be in the range of about 50 mg to 1000 mg daily. For example, a patient being administered a PDE1 inhibitor for a condition according to any of Methods 1-6, et seq., may be administered a PDE1 inhibitor according to Formula, I, Ia, II, III, or IV in an amount of 50 mg to 1000 mg daily, 50 mg to 900 mg daily, 50 mg to 800 mg daily, 50 mg to 700 mg daily, 50 mg to 600 mg daily, 50 mg to 500 mg daily, 50 mg to 400 mg daily, 50 mg to 350 mg daily, 50 mg to 300 mg daily, 50 mg to 250 mg daily, 50 mg to 200 mg daily, 50 mg to 150 mg daily or 50 mg to 100 mg daily.

Compounds of the Disclosure may be administered by any satisfactory route, including orally, parenterally (intravenously, intramuscular or subcutaneous) or transdermally, but are preferably administered orally. In certain embodiments, the Compounds of the Disclosure, e.g., in depot formulation, is preferably administered parenterally, e.g., by injection.

The Compounds of the Disclosure and the Pharmaceutical Compositions of the Disclosure of the Disclosure may be used in combination with one or more additional therapeutic agents, particularly at lower dosages than when the individual agents are used as a monotherapy so as to enhance the therapeutic activities of the combined agents without causing the undesirable side effects commonly occur in conventional monotherapy. Therefore, the Compounds of the Disclosure may be simultaneously, separately, sequentially, or contemporaneously administered with other agents useful in treating disease. In another example, side effects may be reduced or minimized by administering a Compound of the Disclosure in combination with one or more additional therapeutic agents in free or salt form, wherein the dosages of (i) the second therapeutic agent(s) or (ii) both Compound of the Disclosure and the second therapeutic agent, are lower than if the agent/compound are administered as a monotherapy. By way of non-limiting example, such additional therapeutic agents may include ACE inhibitors, Angiotensin II receptor antagonists, calcium channel blockers, etc.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

Pharmaceutical compositions comprising Compounds of the Disclosure may be prepared using conventional diluents or excipients and techniques known in the galenic art. Thus, oral dosage forms may include tablets, capsules, solutions, suspensions and the like.

EXAMPLES

The data below in Examples 1~4 were published in F. Rowther, et al. 2016, Cyclic nucleotide phosphodiesterase-1C (PDE1C) drives cell proliferation, migration and invasion in glioblastoma multiforme cells in vitro. Molecular Carcinogenesis. 55(3): 268-79.

Comparative Example 1: PDE1C Expression in Glioblastoma Multiform Tissue

Short-term cell cultures were prepared from adult glioblastoma multiform (GBM) biopsy tissue as previously described in Lewandowicz G M, et al., Chemosensitivity in childhood brain tumours in vitro: Evidence of differential sensitivity to lomustine (CCNU) and vincristine. Eur J Cancer 2000; 36:1955. The samples were maintained in Hams F10 nutrient mix [Invitrogen, UK] containing 10% foetal calf serum in a 378C non-CO2 incubator. Normal human astrocytes (NHA) [Lonza, UK] and established cell line U251-MG was also included. Consented GBM biopsy samples were taken from the Brain Tumor NW Research Tissue Bank, Preston, UK. Histological evaluation of the GBM tissues were performed at the site and the tumors were classified according to the WHO 2007 grading scheme. Normal human brain controls including total brain cerebellum and foetal corpus callosum were also employed to determine PDE1C expression.

DNA was extracted from the GBM cultures employing QIAmp DNA Mini Kit [Qiagen, UK]. Total RNA was extracted from GBM short-term cultures ($10^6$ cells) or approximately 5 mg of snap frozen biopsy tissues using RNeasy Mini Kit [Qiagen, UK]. DNA and total RNA were quantified using NanoDrop ND-2000 [Thermo Scientific, UK]. cDNA was synthesised from total RNA (500 ng) using QuantiTect Reverse Transcription [Qiagen, UK].

Real-time quantitative PCR was performed from 20 ng/well (96-well) of GBM derived cultures employing PDE1C TaqMan copy number assay with FAM reporter (Hs01364699_cn [Life Technologies, UK]. The locations of the probes were chosen at the same genomic location where aCGH detected focal gain. Taqman assay for TERT was employed [Life Technologies, UK] as endogenous control (VIC reporter) and PDE1C copy number was normalized to its levels. Reference DNA was obtained from mixing equal quantity of male and female genomic DNA [Promega, UK], and was used as a normal control {harboring diploid copies of PDE1C for the assay. QPCR amplifications were performed in triplicate in three independent experiments to obtain accurate copy number data.

For expression analysis, QPCR was carried out using Solaris QPCR PDE1C gene expression assay with FAM reporter [Thermo Scientific, UK] on an ABI 7500 Sequence Detection System [Applied Biosystems, UK]. 2 μL of cDNA was amplified in a 20 mL reaction volume using 1×Solaris qPCR master mix with low ROX [Thermo Scientific, UK] and amplifications were performed in triplicate. The PDE1C expression levels were normalized to GAPDH, and the relative expression was determined using the 24ACT method. Normal Brain controls (Total Brain RNA, Human Cerebellum and corpus callosum) were obtained from Clontech [France].

The results of the QPCR analysis are summarized in Table 1 below.

TABLE 1

QPCR Analysis of PDE1C Copy Number

| Sample | Number of PDE1C Copies (QPCR) | PDE1C Status |
|---|---|---|
| IN1461 | 3.31 ± 0.070 | Gain |
| IN1951 | 2.62 ± 0.210 | Gain |
| IN1528 | 3.67 ± 0.315 | Gain |
| IN1682 | 3.61 ± 0.025 | Gain |
| IN1752 | 2.64 ± 0.261 | Gain |
| IN1612 | 3.03 ± 0.178 | Gain |
| U251-MG | 2.92 ± 0.060 | Gain |
| IN2132 | 2.91 ± 0.216 | Gain |
| IN1760 | 3.03 ± 0.036 | Gain |
| IN1265 | 3.75 ± 0.053 | Gain |
| IN2093 | 3.19 ± 0.259 | Gain |
| IN1979 | 2.66 ± 0.286 | Gain |
| IN1472 | 4.78 ± 0.077 | Gain |
| IN859 | 3.18 ± 0.080 | Gain |
| IN2045 (Control Culture) | 2.30 ± 0.136 | Diploid |
| Reference DNA | 2.00 ± 0.114 | Diploid |

As shown above, QPCR analysis confirms gain of PDE1C in short-term GBM cell cultures. Expression of PDE1C in the short-term cultures using QPCR analysis and association between genomic over-representation and PDE1C expression was evident (FIG. 1) as elevated expression (compared to normal human astrocytes) was present in all tested cell cultures with genomic over-representation, except for the control culture IN2045. In comparison with the control culture, significantly elevated expression in each short-term culture ranging from 23-360 fold (P<0.0001) was observed.

Comparative Example 2: Determining the Role of PDE1C in the Proliferation of GBM siRNA transfections were facilitated using DharmaFECT-1 transfection reagent in a serum containing media and the transfection efficiency was assessed using positive control Cyclophilin-B siRNA [Thermo Scientific, UK]. Cultures were transfected in parallel with non-targeting siRNA pool at the same concentration. Nontargeting siRNA and PDE1C specific siRNA are abbreviated as siNT and siPD. Cells were seeded at 40-50% confluency and incubated for 48 h before commencing transfection. At the end of the initial 48 h incubation, cells were transfected and incubated for 4 d. At day 5, cells were trypsinized and reseeded on to a fresh flask and allowed to attach overnight. The cells were re-transfected at day 6 (either with siNT or siPD) and incubated further for four days before collecting for further experiments. siNT and siPD cells were allowed to grow for 72 h and proliferation assay was performed using SRB as described in Vichai V, Kirtikara K. Sulforhodamine B colorimetric assay for cytotoxicity screening. Nat Protoc 2006; 1:1112-1116. Vinpocetine was dissolved in DMSO and a dose range of serial dilutions from 500 μM to 0.977 UM was used.

Figure 3:
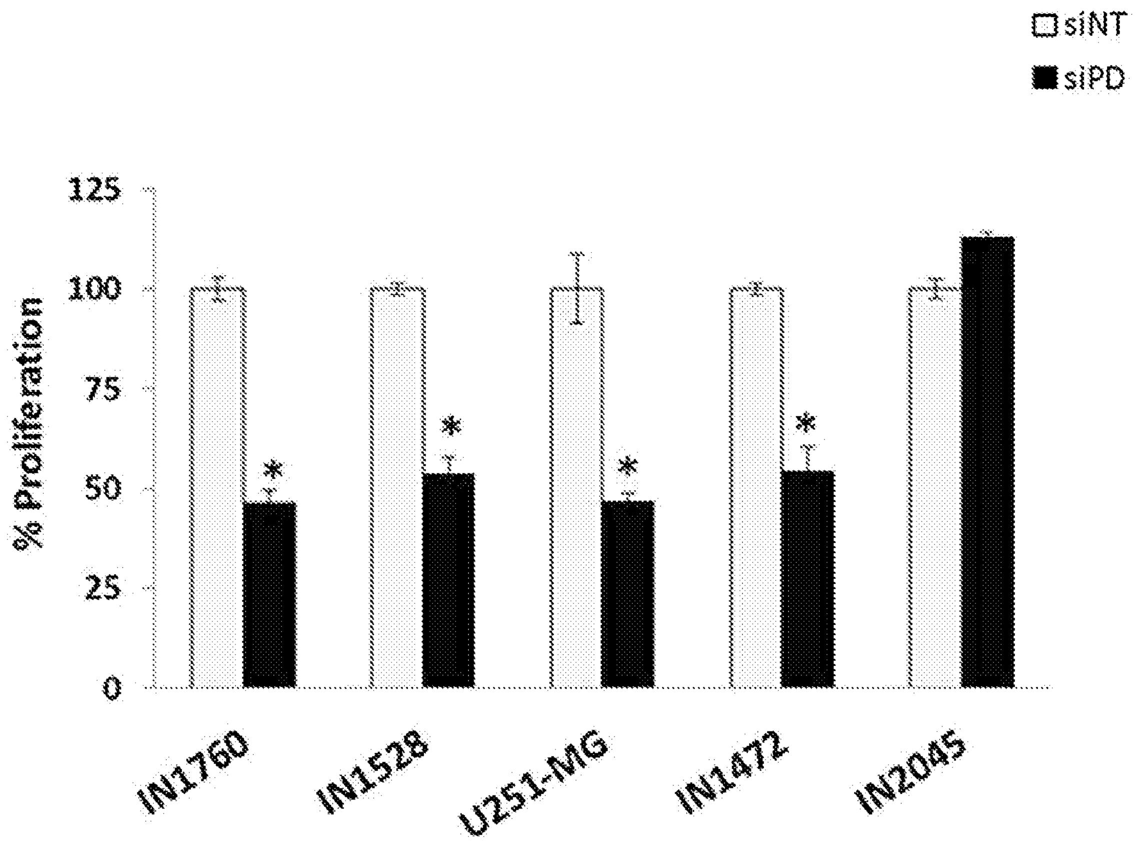
FIG. 3 shows the cell proliferation of tested GBM cell cultures after siRNA mediated depletion of PDE1C.

As shown in FIG. 3, after ceasing transfection, the capacity of the cells to proliferate was assessed. Irrespective of the initial PDE1C expression level, PDE1C depletion consistently reduced proliferation by 45-54% when compared to PDE1C expressing cells (P<0.05) in all cultures except IN2045. cAMP and cGMP activities were also assessed following depletion of PDE1C. It was observed that an increase in the activities of both cAMP and cGMP (P<0.05) was detected in siPD cells compared to siNT cells except in the control culture IN2045.

Comparative Example 3: Determining the Role of PDE1C in the Migration and Invasion of GBM Cells Migration and invasion potential of siNT and siPD was assessed using a CytoSelect 24-well cell migration and invasion assay [Cell Biolabs, Inc., USA]. 20,000 siNT or siPD cells were seeded onto a polycarbonate membrane (8 mM) in a serum free media and serum-containing media was used as a chemo-attractant. At the end of the incubation time, the migrated cells were removed and the non-migratory cells on the membrane were stained using crystal violet and quantified colorimetrically. For the invasion assay, polycarbonate membranes pre-coated with extracellular matrix (ECM) proteins were employed [Cell Biolabs, Inc., USA].

Cell migration was also assessed using CytoSelect 24-well wound healing assay [Cell Biolabs, Inc., USA] following manufacturers' instructions. The % migration was calculated by the formula:

[(cells migrated into the wound field)/(the total number of cells on the slide)]×100.

Migration in siNT was set as 100%. For vinpocetine, the treatment was on-going during the duration of the assay.

Figure 4:
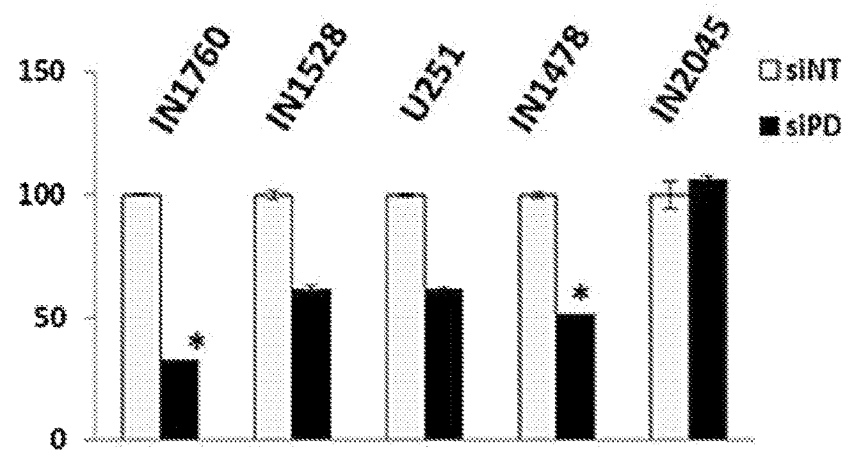
FIG. 4 shows a comparison of cell migration through a polycarbonate membrane of cells modified to specifically target PDE1C and non-targeting cells.
Figure 5:
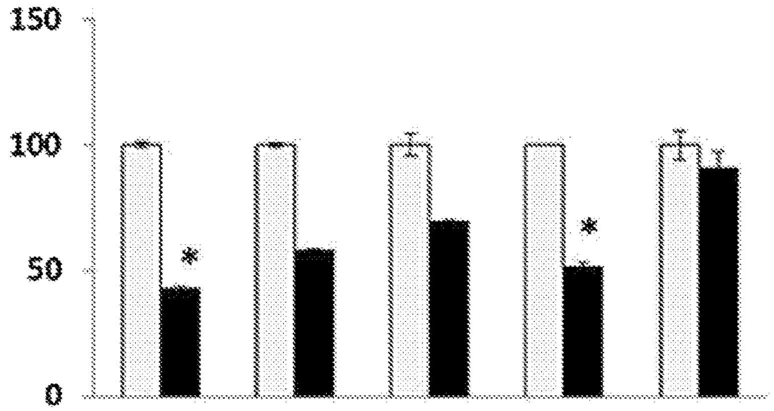
FIG. 5 shows a comparison of cell invasion through an extra-cellular membrane coated polycarbonate membrane of cells modified to specifically target PDE1C and non-targeting cells.
Figure 6:
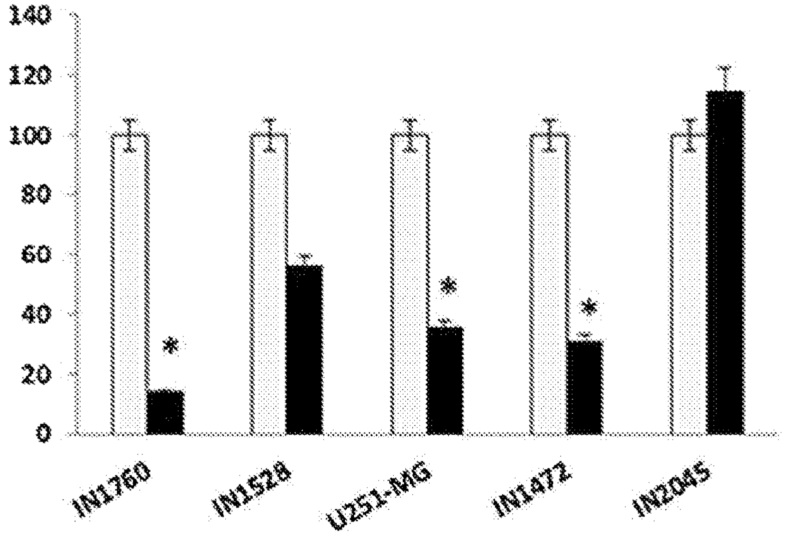
FIG. 6 shows the reduction in the number of cells that migrated within the wound field in cells modified to specifically target PDE1C compared to non-targeting cells in three cultures (IN1472, IN1760, and U251MG).

As illustrated in FIGS. 4 and 5, siPD cells demonstrated reduced capacity to both migrate (through the polycarbonate membrane) and invade (through the ECM coated polycarbonate membrane) when compared to siNT cells. Migrated and invaded cells were quantified and a reduction of migratory and invasive potential of 40-60% was noted in siPD cells compared to siNT. In cultures IN1472 and IN1760, the reduction in cell migration and invasion was statistically significant (P<0.05). It was interesting to note that the relative degree of inhibition of migration and invasion was very similar in each of the individual cultures. Similar to proliferation, there was no inhibition of migration or invasion in siPD IN2045 cells. The results obtained using boyden chamber assays were confirmed in the wound healing assay (FIG. 6) in which the number of cells that migrated within the wound field were significantly reduced in siPD cells compared to siNT cells in three cultures (IN1472, IN1760, and U251MG). These data indicate that PDE1C also acts upstream of migratory and invasive pathways in GBM cells.

Comparative Example 4: Identification of Downstream Effectors of PDE1C

For whole genome expression analysis, 1 mg total RNA was reverse transcribed using MessageAmp™ IIBiotin Enhanced Kit [Ambion; Life Technologies, UK] and hybridised on to the Human Genome U133 Plus 2.0 [Affymetrix, UK]. The arrays were washed in GeneChip Fluidics Station 450 and scanned using GeneChip Scanner 3000 7G [Affymetrix, UK]. Arrays were performed in triplicate for siNT and siPD treatments.

Raw microarray data from Affymetrix CEL files for each of the biological replicates of siNT and siPD were normalised using standard protocol. Array background, Q values, and mean intensities were within acceptable ranges for all arrays. Statistical comparisons and data visualisation were performed using GeneSpring GX12 (Agilent Technologies, UK). Firstly, ≥2-fold change in expression levels in the siPD cells compared to siNT were identified followed by identification of statistically significant genes using 1-Way ANOVA (P<0.05) and a Benjamini and Hochberg False Discovery Rate multiple correction test. Significant biological, process networks, gene ontology (GO) processes and disease markers affected by PDE1C depletion were identified using Metacore™ [GeneGo, Thompson Reuters, USA]. cBIO cancer genomics portal was employed to investigate expression status of PDE1C affected genes in The Cancer Genome Atlas (TCGA) GBM cohorts and to correlate with patient outcome.

Whole genome expression array was performed on cultures, IN1472 and IN1760, where the effect of PDE1C depletion on proliferation, invasion and migration was most profound (FIGS. 2C, 4B, 4D & 4F). Differential expression based on fold change in expression ≥2-fold and a statistical significance of P<0.05 between the siNT and siPD cells identified 565 transcripts (465 genes). For IN1760, 411 differentially expressed genes were detected, of which 146 were up-regulated and 265 were downregulated. In IN1472, 49 genes were upregulated and 5 were down regulated in the siPD cells. Successful knockdown of PDE1C was also established in expression array as it was knockdown by 3-fold and 13-fold for IN1472 and IN1760, respectively. This analysis also established that PDE1C siRNA pool employed in the current study are highly specific to PDE1C as we did not detect any changes in the expression of other PDEs.

In IN1760-siPD cells, the most commonly downregulated genes which showed 3-13 fold downregulation included IL8, PDE1C, KCTD4, PLD5, CXCL6, IL11, B3GALT2, INHBE, OPCML, ELAVL2, and EXT1 (Supplementary File A). Similarly, SPARCL1, APOE, CFI, COMP, FABP3, CLU, FAM107A, PTGDS, CHI3L1, MAN1C1, TDO2, and QPRT showed 4-8 fold upregulation in IN1760-siPD cells. Conversely, in IN1472, PDE1C was the only gene which showed more than 3-fold down-regulation in siPD cells (Supplementary File B). TNFSF15 was also the only gene which showed >3-fold in IN1472-siPD cells. Four genes were differentially expressed in both IN1760-siPD and IN1472-siPD cells, comprising APOE (up-regulated), HSD11B1 (up-regulated), ST6GALNAC5 (down-regulated), and PDE1C (down-regulated).

PDE1C depletion was shown to alter genes involved in important cellular pathways in GBM cells. The genes involved in the most significant pathways affected by PDE1C knockdown were identified as laid out in Tables 2-4 below.

TABLE 2

| Pathways Involving Cell-Matrix Interacations, ECM Remodelling, and Platelet-Endothelium-Leukocyte Interactions | |
|---|---|
| Down-regulated | EDN1, IL1B, IL6, CCL2, TFPI2, THBS1, KAL1, ITGB1, IL8, SERPINE1, COL3A1 |
| Up-regulated | ENG, SERPING1, GPR56, COL4A4, THBD, CXCL5, IL6ST, KDR, CD9 |

TABLE 3

| Pathways Involving Cell Cycle (Mitosis) and Proliferation Control Genes | |
|---|---|
| Down-regulated | NOX4, INHBA, IL18, CDC6, IL6, SMYD2, THBS1, CTNNB1, ITGB1, GNAQ, ADAMTS1, ETS2, IL8, WNTSA, MORC3, BDNF, BRIP1, RERG, SMAD4, BCL2, INHBE, CD274 |
| Up-regulated | HLA-DRA, RARRES3, COX2, PLA2G16, AZGP1, HLA-DRB1, IFITM1, GPNMB, ENG, NDRG2, CDH5, HMOX1, IFI30, AGT, SCG2, INHBA, APOE, FABP3, IGFBP2, ITGA7, COL4A4, EREG, CD9, KRIT1 |

TABLE 4

| Pathways Involving Glioma-Specific Genes | |
|---|---|
| Down-regulated | microRNA 30c-2, PTPRD, CDK5R1, ADAMTS6, DKK3, CALD1, MKI67, VIM, PEG3, SLC7A, KIF3B, MYLK, EPG5, ELAVL2, HMMR, KIF14 |
| Up-regulated | MAFB, CHI3L1, CTSL1, TNXA, TNXB, SOD3, TIMP4, RTN1, CYGB, TNFRSF1B, MGP, MATN2, LAMA4, ABCC3, MDK, SERPINI1 |

It was observed that differentially expressed genes as a consequence of PDE1C depletion strongly correlated with gene expression profiles of TCGA GBM cohorts. In the combined differential gene expression list of siPD IN1760 and IN1472 cells, 32% of PDE1C mediated upregulated genes were down-regulated in TCGA cohorts and 53% of PDE1C mediated down-regulated genes were up-regulated in TCGA cohorts. Within this TCGA gene list, up-regulation of at least one or more of query genes i.e., IL8, CXCL2, FOSB, NFE2L3, SUB1, SORBS2, WNT5A, and MMP1 were associated with worse outcome in patients (P=0.0165) and PDE1C knockdown down-regulated their expression. Hence, although PDE1C expression in isolation is not associated with outcome, the alteration of expression of its downstream effectors as a consequence of PDE1C depletion has potential to improve survival.

Example 1: Determining the Ability of Compounds 1 and 2 to Inhibit the Proliferation, Invasion and Migration of GBM GBM cell cultures are prepared from adult glioblastoma multiform (GBM) biopsy tissue as described in Comparative Examples 2 and 3. Compounds 1 and 2 are administered to cultures to evaluate their effect on the proliferation, invasion and migration of GBM. Compounds 1 and 2 are:

Compound 1

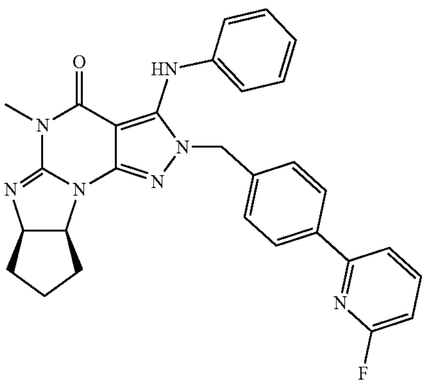

Compound 2

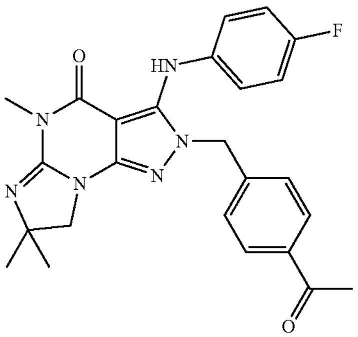

After preparing the cell cultures as discussed above in Comparative Example 2, the capacity of the cells treated with Compound 1 or Compound 2 to proliferate is assessed. Successful runs of the Compounds will show reduced proliferation when compared to PDE1C expressing cells in all cultures except control. Increases in the activities of both cAMP and cGMP will be detected in siPD cells compared to siNT cells except in the control culture.

The capacity of the cells treated with Compound 1 or Compound 2 to migrate and proliferate is also assessed. Successful runs of the Compounds will show reduced migration and/or proliferation in comparison with control cultures.

Example 2: Effect of PDE1 Inhibitors on Various GBM Cell Lines

Seven different cell lines obtained from GBM biopsies were obtained and prepared in short-term pellet cultures, each respectively containing 3-4 million cells. In order to prepare for use in an IMAP assay for PDE activity, the cell pellets were washed once with TBS (150 nM NaCl, 50 mM Tris-HCl, pH 7.4). The pellets were then centrifuged, and the supernatant was removed. The cells were lysed in 0.15 mL lysis buffer (50 mM Tris-HCl, pH 7.4, 5 mM $MgCl_2$, protease inhibitor cocktail). The resulting solution was sonicated twice for a period of 30 seconds and then centrifuged at 15,000 rpm for 15 minutes at 4° C. The supernatant was transferred to a new vessel and frozen immediately. The cells were then assayed for PDE1 expression and sensitivity to inhibition by Compounds 1 and 2 as defined in Example 1. The results are summarized in Table 3 below.

TABLE 3

PDE1 Expression and Sensitivity to Compounds 1 and 2 in Various Cell Populations

| Patent Derived GBM cell lines | PDE1C Expression (fold change compared with normal brain) | $ID_{50}$ Compound 1 (μM) | $ID_{50}$ Compound 2 (μM) |
|---|---|---|---|
| UWLV301 | 75 | 5.4 | 4.73 |
| IN1951 | 64 | 2.04 | 1.03 |
| UWLV304 | 63 | 6.4 | 2.87 |
| IN1528 | 55 | 26.5 | 9.45 |
| U251MG | 45 | 17.8 | 32.0 |
| IN859 | 23 | 34.9 | 9.77 |
| IN2045 | 5 | 18.4 | 12.0 |

As shown above, PDE1C was elevated in all cell lines, with certain cell lines showing as much as a 75-fold increase in PDE1C expression. Both Compound 1 and Compound 2 showed to be similarly efficacious across all tested cell lines.

Further studies were carried out to test the effect of Compounds 1 and 2 on proliferation and survival of the GBM cells. The proliferation of each cell population was tested against Compound 1 and 2 at concentrations of 10 μM and 20 μM. Results on the change in cell population were observed and recorded daily for 8 days. In all cases, treated cell lines proliferated at a slower rate in comparison with the untreated samples. In UWLV301, UWLV304, IN1951, U251MG, and IN2045, the treated GBM cell populations showed an overall decrease by day 8.

Thus, both Compounds 1 and 2 were shown to be highly effective in slowing or eliminating the proliferation of the GBM cell lines.

Example 3: Analysis of GBM Cell Lines for PDE1 Activity, Including Calcium Dependence and Correlation The cell pellets used in Example 2 were assayed to measure calcium dependence of PDE activity as a means to estimate the relative presence of full-length versus truncated enzymes. The truncated enzymes lack the N-terminal regulatory domain and thus are rendered constitutively active in this assay. The assays were prepared according to the protocol of Example 2.

Figure 7:
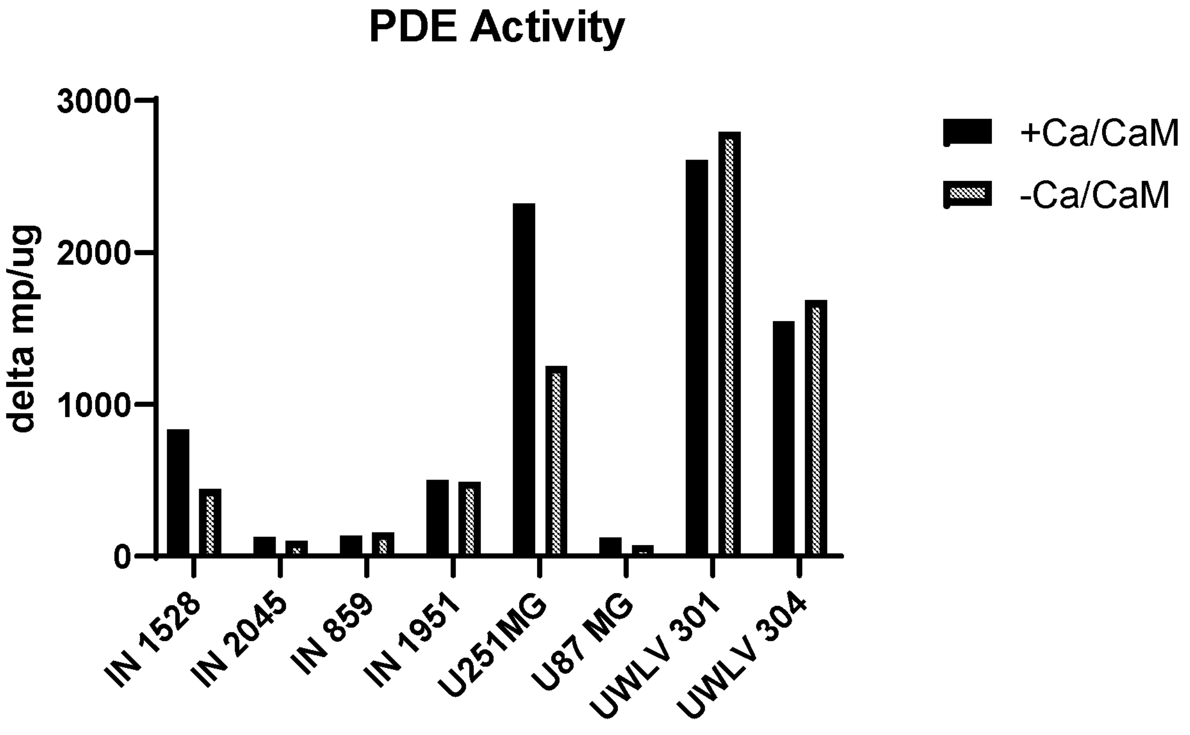
FIG. 7 shows PDE activity in several GBM cell lines measured both in the presence and absence of Ca2+/calmodulin.

Analysis of PDE1 activity the cell lines is shown in FIG. 7. As shown, the UWLV301 and UWLV304 cell lines showed highly active PDE both in the presence and absence of Ca2+/calmodulin. This illustrates that the PDE activities in these cell lines are not calcium dependent. The PDE activity using cAMP as a substrate was not affected by omission of Ca2+/calmodulin in these two cell lines. On the other hand, some of the cell lines, such as IN1528 and U251MG, showed much higher activity levels in the presence of Ca2+/calmodulin than in its absence.

This suggests that GBM progression may cause PDE1 in brain cells to become constitutively activated. Further tests were conducted to investigate this point, which are summarized in Table 4 below. As shown, various cell lines were tested in the presence and absence of Ca2+/calmodulin as well as in the presence of EGTA, a calcium chelator, at various concentrations. These tests confirmed that the UWLV301 and UWLV304 cell lines were constitutively active, i.e., that they remain active without regulation by Ca2+/calmodulin.

TABLE 4

| Percentage of PDE Activity in Various Cell Lines | | | | |
|---|---|---|---|---|
| | Activity (% compared against +CA/CaM baseline) | | | |
| | +Ca/CaM | −Ca/CaM | −Ca/CaM/ 10 μM EGTA | −Ca/CaM/ 40 μM EGTA |
| IN1528 | 100 | 43.18 | 50.08 | 40.02 |
| IN1951 | 100 | 74.16 | 67.77 | 59.37 |
| U251MG | 100 | 37.7 | 39.99 | 23.69 |
| UWLV301 | 100 | 119.73 | 116.45 | 98.9 |
| UWLV304 | 100 | 96.63 | 91.55 | 70.13 |

Further tests were conducted to confirm the PDE isoform primarily associated with GBM cell proliferation. The inhibitory constant ($K_i$) values for Compound 1 on various PDE enzyme families are summarized in Table 5 below.

TABLE 5

| Inhibitory constant values for Compound 1 against PDEs | | |
|---|---|---|
| PDE Target | $K_i$ (μM) | Ratio PDEx/PDE1A |
| PDE1A | 0.000034 | 1 |
| PDE1B | 0.00038 | 11.5 |
| PDE1C | 0.000037 | 1.1 |
| PDE1 (bovine brain) | 0.000058 | 1.7 |
| hPDE2A | >10 | 29,411 |
| hPDE3B | 3.1 | 93,939 |
| hPDE4D | 0.033 | 970 |
| r-bovine PDE5A | 0.63 | 19,090 |
| bovine retina PDE6 | 0.32 | 9696 |
| hPDE7B | 0.36 | 10,909 |
| hPDE8A | 3 | 90,909 |
| hPDE9A | >10 | 294,117 |
| hPDE10A | 1.8 | 54,545 |
| hPDE11A | 1.3 | 39,393 |

An increase in PDE1C expression has previously been observed to be associated with GBM cells. The results here showed the $IC_{50}$ for inhibition of PDE activity in the UWLV301 and UWLV304 cell lines for Compound 1 closely matched the $K_i$ value obtained for purified PDE1C, which supports the idea that the detected PDE activity in these lines is attributed to PDE1C.

Without being bound by theory, it is believed that PDE1C was structural altered, causing the UWLV301 nor UWLV304 cell lines to become constitutively activated. Upon further investigation, neither UWLV301 nor UWLV304 showed detectable full-length PDE1C. During testing, this was substantiated since antibodies to the N-terminus of PDE1C were no longer able to detect PDE1C in those cells that have lost calcium responsivity. On the other hand, the IN1528 and U251MG cell lines, which both remained regulated by Ca2+/calmodulin, showed detectable full-length PDE1C. Thus, these tests suggest that GBM cancer-affected cells could cause dysregulation and structural alterations of PDE1C.

Alternative combinations and variations of the examples provided will become apparent based on the disclosure. It is not possible to provide specific examples for all of the many possible variations of the embodiments described, but such combinations and variations may be claims that eventually issue.

What is claimed is:

1. A method of treating a condition selected from a cancer or tumor comprising administering a pharmaceutically acceptable amount of a PDE1 inhibitor to a subject in need thereof, wherein the PDE1 inhibitor is a compound selected from:

(A) Formula II:

Formula II

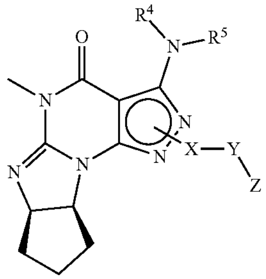

wherein (i) X is methylene;

(ii) Y is phenylene;

(iii) Z is pyridyl optionally substituted with halo;

(iv) $R^4$ is H and $R^5$ is phenyl optionally substituted with halo in free or pharmaceutically acceptable salt form;

(B) Formula 1a:

Formula Ia

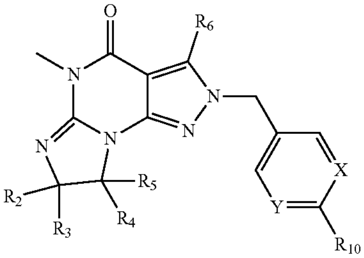

wherein (i) $R_2$ and $R_3$ are each methyl and $R_4$ and $R_5$ are each H;

(ii) $R_6$ is (optionally halo-substituted) phenylamino;

(iii) $R_{10}$ is methylcarbonyl or (optionally halo-substituted) pyridyl; and

X and Y are both C, in free or pharmaceutically acceptable salt form, and wherein the cancer or tumor is a glioma, osteosarcoma, melanoma, leukemia, or neuroblastoma.

2. The method according to claim 1, wherein the PDE1 inhibitor is selected from any of the following

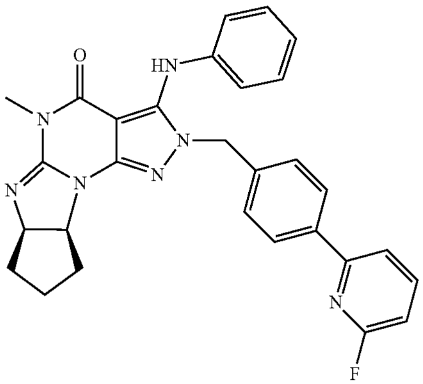
,

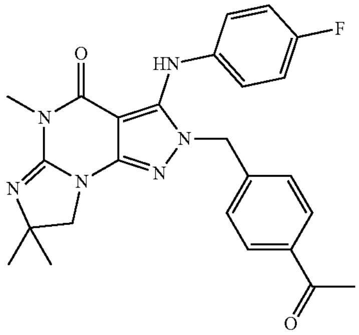
,

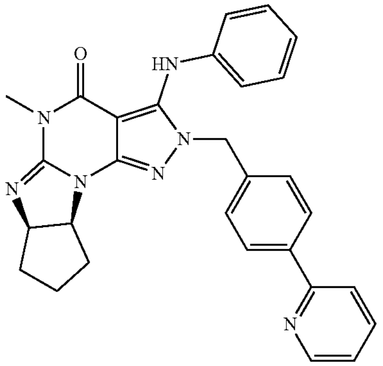

or

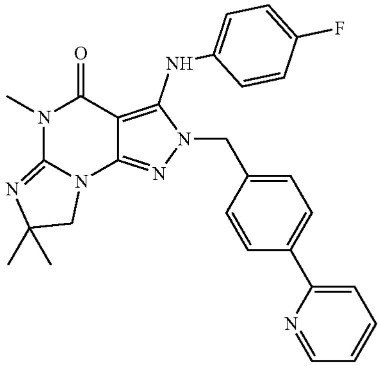

in free or pharmaceutically acceptable salt form.

3. The method according to claim 1, wherein the condition is a glioma.

4. The method according to claim 1, wherein the condition is glioblastoma multiforme.

5. A method of inhibiting the proliferation, migration and/or invasion of a cancer or tumor comprising administering a pharmaceutically acceptable amount of a PDE1 inhibitor to a subject in need thereof, wherein the PDE1 inhibitor is a compound selected from:

(A) Formula II:

Formula II

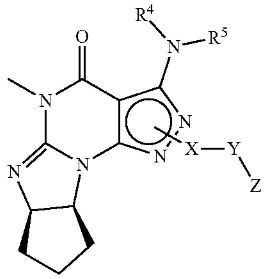

wherein (i) X is methylene;

(ii) Y is phenylene;

(iii) Z is pyridyl optionally substituted with halo (iv) $R^4$ is H and $R^5$ is phenyl optionally substituted with halo in free or pharmaceutically acceptable salt form;

(B) Formula 1a:

Formula Ia

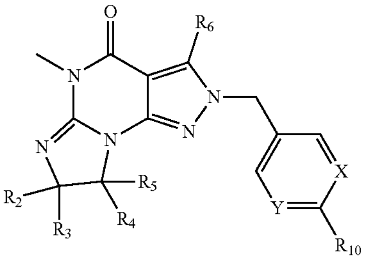

wherein (i) $R_2$ and $R_3$ are each methyl and $R_4$ and $R_5$ are each H;

(ii) $R_6$ is (optionally halo-substituted) phenylamino;

(iii) $R_{10}$ is methylcarbonyl or (optionally halo-substituted) pyridyl; and

X and Y are both C, in free or pharmaceutically acceptable salt form, and wherein the cancer or tumor is a glioma, osteosarcoma, melanoma, leukemia, or neuroblastoma.

6. The method according to claim 5, wherein the PDE1 inhibitor is selected from any of the following

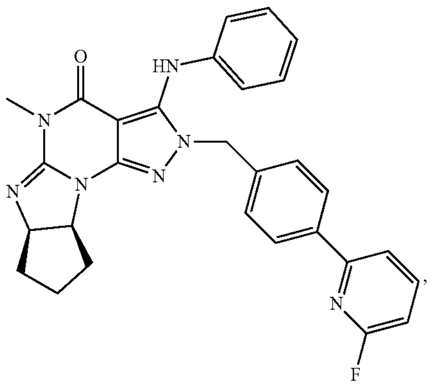
,

-continued

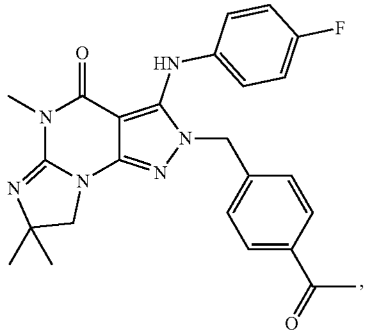

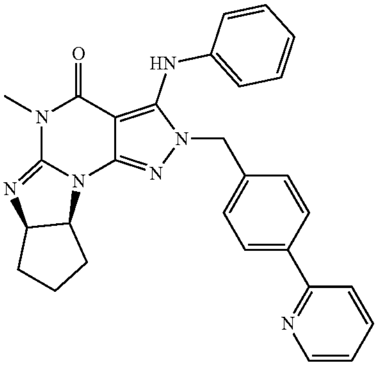

or

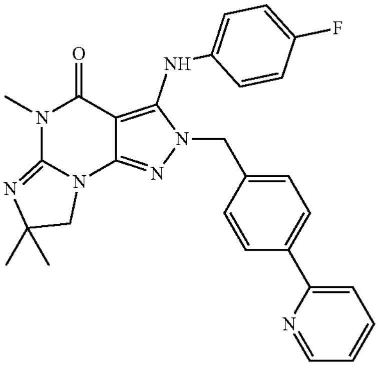

in free or pharmaceutically acceptable salt form.

7. The method according to claim 5, wherein the condition is a glioma.

8. The method according to claim 7, wherein the condition is glioblastoma multiforme.

9. The method according to claim 1, wherein the PDE1 inhibitor is

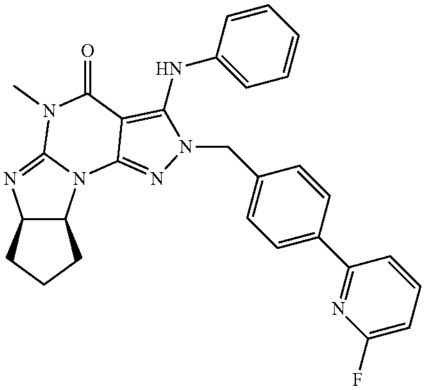 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

10. The method according to claim 1, wherein the PDE1 inhibitor is,

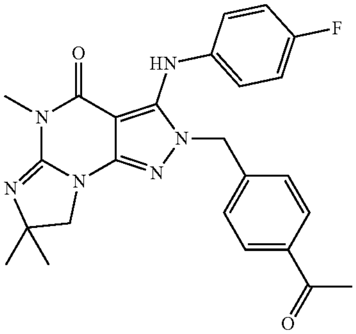 [SMILES: CC(=O)c1ccc(Cn2nc3c(c2Nc2ccc(F)cc2)C(=O)N(C)C2=NC(C)(C)CN23)cc1]

free or pharmaceutically acceptable salt form.

11. The method according to claim 1, wherein the PDE1 inhibitor is

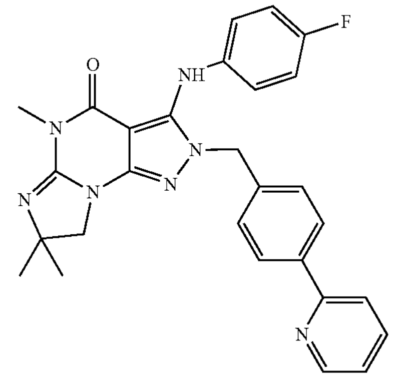 [SMILES: CN1C(=O)c2c(nn(Cc3ccc(-c4ccccn4)cc3)c2Nc2ccc(F)cc2)N2CC(C)(C)N=C12]

in free or pharmaceutically acceptable salt form.

12. The method according to claim 5, wherein the PDE1 inhibitor is

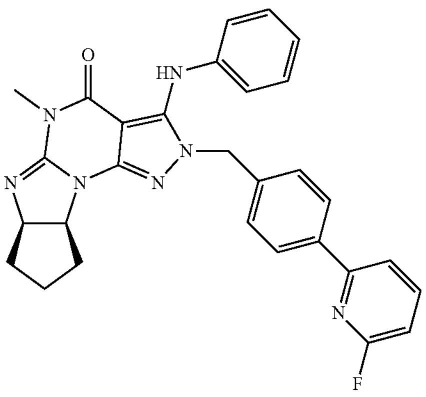 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

13. The method according to claim 5, wherein the PDE1 inhibitor is

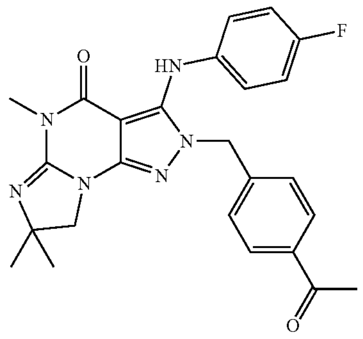 [SMILES: CC(=O)c1ccc(Cn2nc3c(c2Nc2ccc(F)cc2)C(=O)N(C)C2=NC(C)(C)CN23)cc1]

free or pharmaceutically acceptable salt form.

14. The method according to claim 5, wherein the PDE1 inhibitor is

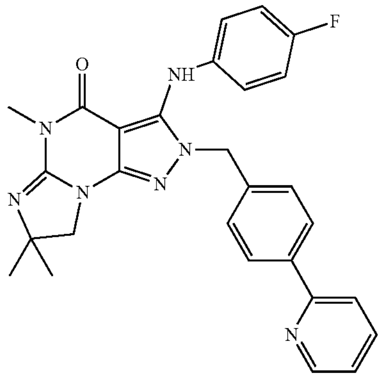 [SMILES: CN1C(=O)c2c(nn(Cc3ccc(-c4ccccn4)cc3)c2Nc2ccc(F)cc2)N2CC(C)(C)N=C12]

in free or pharmaceutically acceptable salt form.

* * * * *